United States Patent [19]

Kaldor et al.

[11] Patent Number: 5,719,287

[45] Date of Patent: Feb. 17, 1998

[54] INTERMEDIATES FOR INHIBITORS OF HIV PROTEASE AND METHOD OF PREPARATION THEREOF

[75] Inventors: Stephen W. Kaldor; Marlys Hammond, both of Indianapolis, Ind.

[73] Assignee: Eli Lilly and Company, Indianapolis, Ind.

[21] Appl. No.: 449,176

[22] Filed: May 24, 1995

Related U.S. Application Data

[60] Division of Ser. No. 875,908, Apr. 29, 1992, Pat. No. 5,508,407, which is a continuation-in-part of Ser. No. 727,787, Jul. 10, 1991, abandoned.

[51] Int. Cl.[6] .................. C07D 215/00; C07D 309/32; C07D 401/06; C07C 221/00
[52] U.S. Cl. .................. 546/174; 540/484; 540/485; 546/226; 546/243; 548/530; 548/543; 564/342; 549/54; 549/74; 549/467; 549/491
[58] Field of Search .................. 564/342; 548/543, 548/530; 546/243, 226, 174; 549/58, 74, 467, 491; 540/484, 485

[56] References Cited

FOREIGN PATENT DOCUMENTS

| | | |
|---|---|---|
| 0 337 714 | 10/1989 | European Pat. Off. . |
| 0 346 847 | 12/1989 | European Pat. Off. . |
| 0 356 223 | 2/1990 | European Pat. Off. . |
| 0 361 341 | 4/1990 | European Pat. Off. . |
| 0 402 646 | 12/1990 | European Pat. Off. . |
| 0 432 695 | 6/1991 | European Pat. Off. . |
| 0 434 365 | 6/1991 | European Pat. Off. . |

OTHER PUBLICATIONS

Snieckus, *Chemical Reviews*, 90, 879–933 (1990).
Beak, et al., *Tetrahedron*, 39, 1983–1989 (1983).
Nahm and Weinreb, *Tetrahedron Letters*, 22, 3815–3818 (1981).
Fehrentz and Castro, *Synthesis*, No. 8, 676–678 (1983).
Roberts, N.A. et al., *Science*, 248, 358–361 (1990).
Tam, T.F. et al., *Journal of Medicinal Chemistry*, 35(7), 1318–1320 (3 Apr. 1992).
Young, S.G., et al., *Journal of Medicinal Chemistry*, 35(10), 1702–1709 (15 May 1992).
Huff, J.R., *Journal of Medicinal Chemistry*, 34(8), 2305–2314 (Aug. 1991).

*Primary Examiner*—David B. Springer
*Attorney, Agent, or Firm*—Joseph A. Jones; Janet T. McClain

[57] ABSTRACT

The present invention provides novel HIV protease inhibitors, pharmaceutical formulations containing those compounds and methods of their use.

2 Claims, No Drawings

INTERMEDIATES FOR INHIBITORS OF HIV PROTEASE AND METHOD OF PREPARATION THEREOF

CROSS REFERENCE TO RELATED APPLICATION

This application is a division of application Ser. No. 07/875,908, filed Apr. 29, 1992, now U.S. Pat. No. 5,508,409 which is a continuation-in-part of application Ser. No. 07/727,787, filed Jul. 10, 1991 (now abandoned).

BACKGROUND OF THE INVENTION

A retrovirus designated human immuno-deficiency virus (HIV) is the causative agent of the complex disease termed Acquired Immune Deficiency Syndrome (AIDS), and is a member of the lentivirus family of retroviruses (M. A. Gonda, F. Wong-Staal NR. C. Galo, "Sequence Homology and Morphological Similarity of HTLV III And Visna Virus, A Pathogenic Lentivirus", Science, 227, 173, (1985); and P. Sonigo and N. Alizon, et al., "Nucleotide Sequence of the Visna Lentivirus: Relationship to the AIDS Virus", Cell, 42,369, (1985)). The complex disease AIDS includes progressive destruction of the immune system and degeneration of the central and peripheral nervous systems. The HIV virus was previously known or referred to as LAV, HTLV-III, or ARV.

A common feature of retrovirus replication is the post-translational processing of precursor polyproteins by a virally encoded protease to generate mature viral proteins required for viral assembly and function. Interruption of this processing appears to prevent the production of normally infectious virus. Unprocessed structural proteins also have been observed in clones of non-infectious HIV strains isolated from human patients. The results suggest that inhibition of the HIV protease represents a viable method for the treatment of AIDS and the prevention or treatment of infection by HIV.

The HIV genome encodes structural protein precursors known as gag and pol, which are processed to afford the protease, reverse transcriptase and endonuclease/integrase. The protease further cleaves gag and gag-pol polyproteins to yield mature structural proteins of the virus core.

Considerable efforts are being directed toward the control of HIV by means of the structural protein precursors which are processed to yield the retroviral protease, reverse transcriptase and endonuclease/integrase. For example, the currently used therapeutic, AZT, is an inhibitor of the viral reverse transcriptase (H. Mitsuya, NS. Broder, "Inhibition of the In Vitro Infectivity in Cytopathic Effects of HTLV III", Proc. Natl. Acad. Sci. USA, 83, 1911 (1986).

Research efforts have also been directed toward HIV protease inhibitors. For example, EPA 361 341; EPA 346 847; EPA 402 646; and EPA 337 714 all disclose compounds which are said to be useful as HIV protease inhibitors.

Unfortunately, many of the known compounds suffer from toxicity problems, lack of bioavailability or are short lived in vivo.

Despite the recognized therapeutic potential associated with a protease inhibitor and the research efforts expended thus far, a viable therapeutic agent has not yet emerged.

Accordingly, a primary object of the present invention is to provide novel HIV protease inhibitors which are useful in the treatment of AIDS.

A further object of the present invention is to provide therapeutic compositions that are of value in the prevention and/or treatment of infection by HIV and the treatment of the resulting acquired immune deficiency syndrome.

Still another object is to provide methods for the prevention and/or treatment of infection by HIV and the resulting acquired immune deficiency syndrome.

Other objects, features, and advantages will become apparent to those skilled in the art from the following description and claims.

SUMMARY OF THE INVENTION

The present invention relates to compounds and pharmaceutically acceptable salts thereof that inhibit the protease encoded by human immunodeficiency virus (HIV) type 1 (HIV-1) and type 2 (HIV-2). These compounds are useful in the prevention of infection by HIV, the treatment of infection by HIV and/or the treatment of the resulting acquired immune deficiency syndrome (AIDS) either as compounds, pharmaceutically acceptable salts, pharmaceutical composition ingredients, whether or not in combination with other anti-virals, immunomodulators, antibiotics or vaccines. Methods of treating AIDS, methods of preventing infection by HIV and methods of treating infection by HIV are also disclosed.

The compounds of the present invention are those having the Formula:

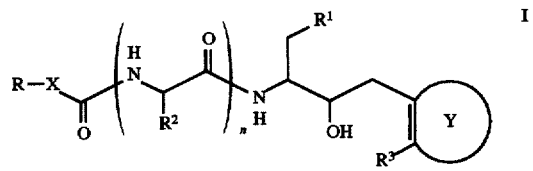

where:

R is $C_5$–$C_7$ cycloalkyl, heterocycle, aryl or unsaturated heterocycle;

X is a bond, $(-CH_2-)_q$, $-O-(-CH_2-)_q-$, $-(-CH_2-)_q-O-$ or $-N(R^5)(CH_2-)_m-$;

n is 0, 1, or 2;

q is 1, 2, 3 or 4;

$R^1$ is aryl or $C_5$–$C_7$ cycloalkyl;

$R^2$ is an amino acid side chain, unsaturated heterocycle, unsaturated heterocycle ($C_1$–$C_4$ alkanediyl), $C_1$–$C_4$ alkylaminocarbonyl ($C_1$–$C_4$ alkanediyl), or a group having the structure $-CH_2-C(O)-NR^4-X-R$ or $-CH_2-R$;

Y is an azyl or unsaturated heterocycle;

$R^3$ is a group having the structure:

$$-C(O)-NR^4R^4 \quad\quad 1)$$

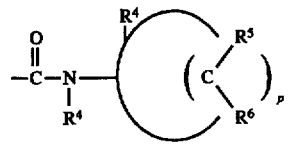  2)

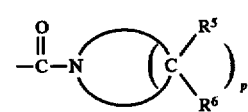  3)

$$-N-C(O)-R^6; \quad\quad 4)$$
$$R^5$$

$$-N-C(O)-NR^4R^4; \quad\quad 5)$$
$$R^4$$

-continued

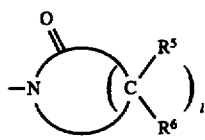

where:

l is 3, 4 or 5;

m at each occurrence is independently 0, 1, 2, or 3;

p is 4 or 5;

$R^4$ at each occurrence is independently hydrogen, $C_1$–$C_6$ alkyl or hydroxy($C_1$–$C_4$)alkanediyl;

$R^5$ and $R^6$ are independently selected from hydrogen, hydroxy, $C_1$–$C_6$ alkyl, $C_1$–$C_6$ alkoxy, amino, $C_1$–$C_4$ alkylamino, hydroxy($C_1$–$C_4$)alkanediyl, carboxy, ($C_1$–$C_4$ alkoxy)carbonyl, aminocarbonyl, $C_1$–$C_4$ alkylaminocarbonyl, aryl, heterocycle or unsaturated heterocycle; or a pharmaceutically acceptable salt or solvate thereof.

This invention also provides pharmaceutical formulations which comprise a compound of Formula I, or the pharmaceutically acceptable salt or solvate thereof, in association with a pharmaceutically acceptable carrier, diluent or excipient.

A further embodiment of the present invention is a method for inhibiting HIV protease. More particularly, the present invention contemplates a method for treating infection by HIV comprising administering to a mammal in need of HIV inhibition, an HIV inhibiting dose of a compound of Formula I or a pharmaceutically acceptable salt or solvate thereof.

A further embodiment of the present invention is a class of novel intermediates useful for preparing compounds of Formula I and a process for preparing said intermediates. The intermediates have the Formula

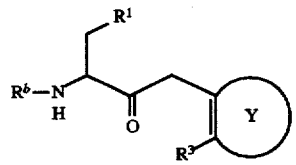

II where $R^1$ is aryl or $C_5$–$C_7$ cycloalkyl;

$R^b$ is hydrogen or an amino protecting group;

Y is aryl or unsaturated heterocycle;

$R^3$ is a group selected from:

—C(O)—NR$^4$R$^4$    1)

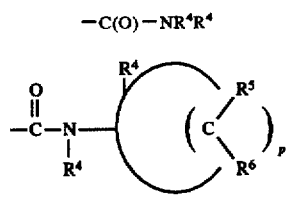    2)

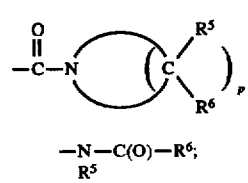    3)

—N—C(O)—R$^6$;    4)
R$^5$

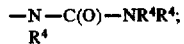    5)

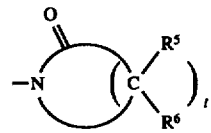    6)

where $R^4$, $R^5$, $R^6$, l and p are as defined above for Formula I or a pharmaceutically acceptable salt or solvate thereof.

The process aspect of the present invention is a process for preparing the ketone intermediates of Formula II which comprises:

a) reacting a compound having the formula:

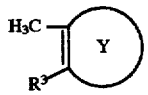

where $R^3$ and Y are as defined above for Formula I with a $C_1$–$C_4$ alkyl lithium or lithium di($C_1$–$C_4$ alkyl) amide base either in the presence or absence of a tetramethyl ($C_1$–$C_4$ alkylene) diamine catalyst in an aprotic solvent to afford the corresponding anion; and b) reacting the anion from (a) with an amide having the Formula

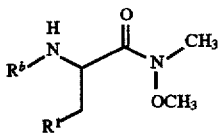

where $R^b$ and $R^1$ are as defined above for Formula I in an aprotic solvent to afford said ketone intermediate.

DETAILED DESCRIPTION OF THE INVENTION

The term "alkyl" by itself or as part of another substituent, unless otherwise stated, includes straight or branched chain groups such as methyl, ethyl, n-propyl, isopropyl, n-butyl, t-butyl, isobutyl, sec-butyl, and where indicated, higher homologs and isomers such as n-pentyl, n-hexyl, 2-methylpentyl and the like. The term "alkoxy" represents an alkyl group of the stated number of carbon atoms attached through an oxygen bridge such as methoxy, ethoxy, n-propoxy, isopropoxy and the like. The term "hydroxy ($C_1$–$C_4$) alkanediyl" means a divalent alkyl group having the stated number of carbon atoms bonded to a hydroxy group, such as hydroxymethyl, hydroxyethyl, hydroxypropyl, and hydroxybutyl. The term "$C_1$–$C_4$ alkylamino" means a group (—NH($C_1$–$C_4$ alkyl)) where the alkyl group has the stated number of carbon atoms. The term "$C_1$–$C_4$ dialkylamino" means a group (—N($C_1$–$C_4$ alkyl)$_2$) where each alkyl group, independently, has the stated number of carbon atoms. The term "cycloalkyl" means a saturated ring group having the stated number of carbon atoms such as cyclopentyl, cyclohexyl and cycloheptyl.

The term "heterocycle" means an unsubstituted or substituted stable 5- to 7-membered monocyclic and stable 7- to 10-membered bicyclic heterocyclic ring which is saturated and which consists of carbon atoms and from one to three heteroatoms selected from the group consisting of N, O, S, and wherein the nitrogen and sulfur heteroatoms may optionally be oxidized, and the nitrogen heteroatom may optionally be quaternized and including a bicyclic group in which any of the above-defined heterocyclic rings is fused to a benzene ring. The heterocyclic ring may be attached at any heteroatom or carbon atom which affords a stable structure. The heterocycle is unsubstituted or substituted with 1, 2, or 3 substituents independently selected from halo, $C_1$-$C_5$ alkyl, $C_1$-$C_5$ alkoxy, carboxy, ($C_1$-$C_4$ alkoxy)carbonyl, aminocarbonyl, $C_1$-$C_4$ alkylaminocarbonyl, amino, $C_1$-$C_4$ alkylamino, $C_1$-$C_4$ dialkylamino or a group —$(CH_2)_q$—$R^7$ where q is 1, 2, 3, or 4 and $R^7$ is hydroxy, $C_1$-$C_4$ alkoxy, carboxy, $C_1$-$C_4$ alkoxycarbonyl, amino, aminocarbonyl, $C_1$-$C_4$ alkylamino or $C_1$-$C_4$ dialkylamino.

The term "unsaturated heterocycle" means an unsubstituted or substituted stable 5- to 7-membered monocyclic and stable 7- to 10-membered bicyclic heterocyclic ring which has one or more double bonds and which consists of carbon atoms and from one to three heteroatoms selected from the group consisting of N, o, S, and wherein the nitrogen and sulfur heteroatoms may optionally be oxidized, and the nitrogen heteroatom may optionally be quaternized and including a bicyclic group in which any of the above-defined heterocyclic rings is fused to a benzene ring. The unsaturated heterocyclic ring may be attached at any heteroatom or carbon atom which affords a stable structure. The unsaturated heterocycle is unsubstituted or substituted with 1, 2, or 3 substituents independently selected from halo, $C_1$-$C_5$ alkyl, $C_1$-$C_5$alkoxy, carboxy, ($C_1$-$C_4$ alkoxy)carbonyl, aminocarbonyl, $C_1$-$C_4$ alkylaminocarbonyl, amino, $C_1$-$C_4$ alkylamino, $C_1$-$C_4$ dialkylamino or a group —$(CH_2)_q$—$R^7$ where q is 1, 2, 3, or 4 and $R^7$ is hydroxy, $C_1$-$C_4$ alkoxy, carboxy, $C_1$-$C_4$ alkoxycarbonyl, amino, aminocarbonyl, $C_1$-$C_4$ alkylamino or $C_1$-$C_4$ dialkylamino.

Examples of such heterocycles and unsaturated heterocycles include piperidinyl, piperazinyl, 2-oxopiperazinyl, 2-oxopiperidinyl, 2-oxo-pyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazolyl, benzopyranyl, benzothiazolyl, benzoazolyl, furyl, tetrahydrofuryl, tetrahydropyranyl, thienyl, benzothienyl, thiamorpholinyl, thiamorpholinylsulfoxide, thiamorpholinylsulfone, oxadiazolyl, triazolyl, tetrahydroquinolinyl and tetrahydrisoquinolinyl.

The term "aryl" means unsubstituted or substituted phenyl or unsubstituted or substituted naphthyl. The phenyl or naphthyl ring is unsubstituted or substituted with 1, 2, or 3 substituents independently selected from halo, $C_1$-$C_5$ alkyl, $C_1$-$C_5$ alkoxy, carboxy, ($C_1$-$C_4$ alkoxy)carbonyl, aminocarbonyl, $C_1$-$C_4$ alkylaminocarbonyl, amino, $C_1$-$C_4$ alkylamino, $C_1$-$C_4$ dialkylamino, benzyloxy or a group —$(CH_2)_q$—$R^7$ where q is 1, 2, 3, or 4 and $R^7$ is hydroxy, $C_1$-$C_4$ alkoxy, carboxy, $C_1$-$C_4$ alkoxycarbonyl, amino, aminocarbonyl, $C_1$-$C_4$ alkylamino or $C_1$-$C_4$ dialkylamino. The term "halogen" and "halo" mean any of chloro, bromo, fluoro and iodo.

The third group in the definition of $R^3$ includes unsubstituted and substituted piperidinyl, and unsubstituted and substituted pyrrolidinyl where the substituents are selected from those defined for $R^5$ and $R^6$ which affords a sterically feasible stable structure.

The term "amino acid side chains" means the distinctive atom or group bonded to an α-carbon atom also having bonded thereto a carboxyl group and an amino group. These side chains are selected from those found on D and L:

| | |
|---|---|
| Alanine | Ala |
| Arginine | Arg |
| Asparagine | Asn |
| Aspartic acid | Asp |
| Cysteine | Cys |
| Glutamine | Gln |
| Glutamic acid | Glu |
| Glycine | Gly |
| Histidine | His |
| Isoleucine | Ile |
| Leucine | Leu |
| Lysine | Lys |
| Methionine | Met |
| Phenylalanine | Phe |
| Proline | Pro |
| Serine | Ser |
| Threonine | Thr |
| Tryptophan | Trp |
| Tyrosine | Tyr |
| Valine | Val |

The term "amino-protecting group" as used in the specification refers to substituents of the amino group commonly employed to block or protect the amino functionality while reacting other functional groups on the compound. Examples of such amino-protecting groups include the formyl group, the trityl group, the phthalimido group, the trichloroacetyl group, the chloroacetyl, bromoacetyl and iodoacetyl groups, urethane-type blocking groups such as benzyloxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxy-carbonyl, 2-(4-xenyl)isopropoxycarbonyl, 1,1-diphenyleth-1-yloxycarbonyl, 1,1-diphenylprop-1-yloxycarbonyl, 2-phenylprop-2-yloxycarbonyl, 2-(p-toluyl)prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl)ethoxycarbonyl, 2(methylsulfonyl)ethoxycarbonyl, 2-(triphenylphosphino)ethoxycarbonyl, fluorenylmethoxycarbonyl ("FMOC"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy)benzyloxycarbonyl, isobronyloxycarbonyl, 1-piperidyloxycarbonyl and the like; the benzoylmethylsulfonyl group, the 2-(nitro)phenylsulfenyl group, the diphenylphosphine oxide group and like amino-protecting groups. The species of amino-protecting group employed is not critical so long as the derivatized amino group is stable to the condition of subsequent reaction(s) on other positions of the intermediate molecule and can be selectively removed at the appropriate point without disrupting the remainder of the molecule including any other amino-protecting group(s). Preferred amino-protecting groups are t-butoxycarbonyl, and benzyloxycarbonyl. Further examples of groups referred to by the above terms are described by J. W. Barton, "Protective Groups in Organic Chemistry", J. G. W. McOmie, Ed., Plenum Press, New York, N.Y., 1973, Chapter 2, and T. W. Greene, "Protective Groups in Organic Synthesis", John Wiley and sons, New York, N.Y., 1981, Chapter 7.

The compounds of the present invention have at least three asymmetric centers denoted by an asterisk in Formula IA below.

$$R-X \left( \underset{O}{\overset{H}{\underset{|}{N}}} \overset{*}{\underset{R^2}{C}} \overset{O}{\underset{||}{C}} \right) \underset{H}{\overset{R^1}{\underset{|}{N}}} \overset{*}{C} \overset{*}{C} \underset{OH}{\overset{}{C}} \underset{R^3}{\overset{}{Y}} \quad \text{IA}$$

As a consequence of these chiral centers, the compounds of the present invention occur as racemates, racemic mixtures and as individual diastereomers. All asymmetric forms, individual isomers and combinations thereof, are within the scope of the present invention.

As mentioned above, the invention includes pharmaceutically acceptable salts of the compounds defined by the above formula. Although generally neutral, a particular compound of this invention can possess a sufficiently acidic, a sufficiently basic, or both functional groups, and accordingly react with any of a number of nontoxic inorganic bases, and nontoxic inorganic and organic acids, to form a pharmaceutically acceptable salt. Acids commonly employed to form acid addition salts are inorganic acids such as hydrochloric acid, hydrobromic acid, hydroiodic acid, sulfuric acid, phosphoric acid, and the like, and organic acids such as p-toluene-sulfonic, methanesulfonic acid, oxalic acid, p-bromo-phenylsulfonic acid, carbonic acid, succinic acid, citric acid, benzoic acid, acetic acid, and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, g-hydroxybutyrate, glycollate, tartrate, methanesulfonate, propanesulfonate, naphthalene-1-sulfonate, napththalene-2-sulfonate, mandelate and the like. Preferred pharmaceutically acceptable acid addition salts are those formed with mineral acids such as hydrochloric acid and hydrobromic acid, and those formed with organic acids such as maleic acid and methanesulfonic acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

Preferred compounds of this invention are those of Formula I where

R is aryl or unsaturated heterocycle;

X is a bond, —O—(—CH$_2$—)$_q$—, or —(—CH$_2$—)$_q$—O—;

q is 1 or 2;

n is 1 or 2;

R$^1$ is aryl;

R$^2$ is an amino acid side chain or unsaturated heterocycle (C$_1$–C$_4$ alkanediyl);

Y is aryl;

R$^3$ is —C(O)—NR$_4$R$^4$ or —N(R$_5$)C(O)—R$^6$ where R$^4$, R$^5$ and R$^6$ are independently and at each occurrence hydrogen or C$_1$–C$_6$ alkyl; or a pharmaceutically acceptable salt or solvate thereof.

Alternatively, preferred compounds of this invention are those of Formula I where:

R is aryl or unsaturated heterocycle;

X is a bond, (—CH$_2$—)$_q$, —O—(—CH$_2$—)$_q$—, or —(—CH$_2$—)$_q$—O—;

q is 1 or 2;

n is 1 or 2;

R$^1$ is aryl;

R$^2$ is an amino acid side chain, unsaturated heterocycle (C$_1$–C$_4$ alkanediyl) or —CH$_2$—C(O)—NR$^4$—X—R;

Y is aryl;

R$^3$ is —C(O)—NR$_4$R$^4$ or —N(R$_5$)C(O)—R$^6$ where R$^4$, R$^5$ and R$^6$ are independently and at each occurrence hydrogen or C$_1$–C$_6$ alkyl; or a pharmaceutically acceptable salt or solvate thereof.

More preferred compounds are those of Formula I where:

R is naphthyl, quinoxalinyl or quinolinyl, each of said radicals unsubstituted or substituted with one or two C$_1$–C$_4$ alkyl groups;

X is a bond, —OCH$_2$——CH$_2$O—;

n is 1;

R$^1$ is phenyl;

R$^2$ is —CH$_2$—C(O)—NH$_2$;

Y is phenyl, unsubstituted or substituted with C$_1$–C$_4$ alkyl; or the pharmaceutically acceptable salt or solvate thereof.

Particularly preferred compounds are those of Formula IB:

[Structure of Formula IB showing a substituted quinoline connected via amide linkages to a peptide backbone with phenyl, NH$_2$-C(=O)-CH$_2$-, OH, and a benzamide group bearing R$^4$ substituents]

where at each occurence R$^4$ is independently hydrogen or C$_1$–C$_4$ alkyl; or a pharmaceutically acceptable salt or solvate thereof.

The compounds of the present invention, or their precursors, are prepared using procedures known to those of ordinary skill in art. More particularly, the compounds of Formula I where R$^3$ is bonded through a carbonyl group (groups 1 through 3 in the definition of R$^3$) are prepared according to the procedures shown below in Scheme 1 and as described following Scheme 1.

Scheme 1:

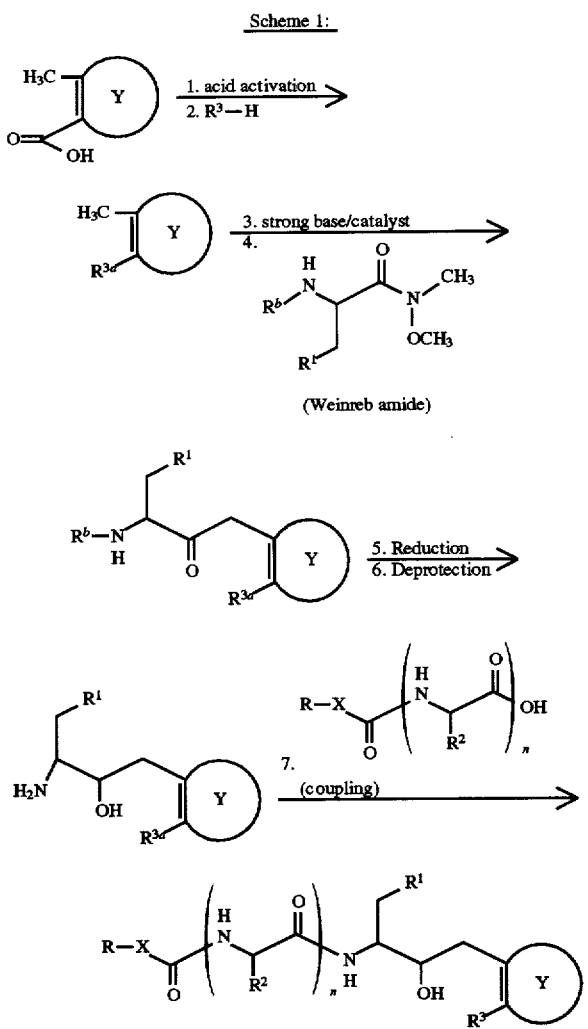

(Weinreb amide)

where:

R, X, n, $R^1$, $R^2$, and Y are as defined above for Formula I, $R^b$ is an amino protecting group, and $R^{3a}$ is group 1 through 3 of $R^3$ as defined above for Formula I.

In Scheme 1, a suitable aryl or unsaturated heterocycle carboxylic acid is activated, that is, converted, in Reaction 1 to the corresponding acid chloride or acid bromide by reaction with thionyl chloride, thionyl bromide, phosphorous trichloride, phosphorous tribromide, phosphorous pentabromide or phosphorous pentachloride according to procedures and under conditions well known to those skilled in the art. The acid chloride or acid bromide afforded by Reaction 1 can be isolated or further reacted as shown in Reaction 2. Suitable aryl or unsaturated heterocycle carboxylic acid compounds are commercially available or prepared by standard procedures well known to those skilled in the art.

In Reaction 2, the acid chloride or acid bromide is reacted with a primary or secondary amine having the formula $R^3$—H where $R^3$ is as defined above for Formula I in a nonpolar aprotic solvent or mixture of solvents in the presence or absence of an acid scavenger at a temperature of from about −20° C. to about 25° C. to afford the corresponding amide. Suitable solvents for this reaction include ethers and chlorinated hydrocarbons, preferably diethyl ether, chloroform, or methylene chloride. Preferably, this reaction is carried out in the presence of an acid scavenger such as a tertiary amine, preferably triethyl amine. The amide afforded by this reaction may be isolated or further reacted as shown in Reaction 3.

In Reaction 3, the amide is reacted with a strong base in the presence of a catalyst in an aprotic solvent at a temperature of from about −78° C. to about 0° C. to afford the corresponding anion which is reacted with a Weinreb Amide in an aprotic solvent at a temperature from about −80° C. to about −40° C. to afford a ketone which may be isolated or further reacted as shown in Reaction 5. Suitable bases for Reaction 3 include lithium amide bases and alkyl lithium bases, preferably $C_1$–$C_4$ alkyl lithium bases and lithium di($C_1$–$C_4$ alkyl)amide bases. Suitable solvents for Reaction 3 are ethers and preferably tetrahydrofuran (THF). Suitable catalysts for Reaction 3 are tetramethyl ($C_1$–$C_4$ alkylene) diamines and preferably tetramethylethylenediamine. In Reaction 4 about 2 equivalents of the anion are used per equivalent of Weinreb Amide.

In Reaction 5 the ketone is reduced using a suitable reducing agent in a protic solvent at a temperature of from about −25° C. to about 25° C. to the corresponding alcohol. Suitable reducing agents for this reaction include sodium borohydride, lithium borohydride, diisobutylaluminum hydride, and sodium bis(2-methoxyethoxy)aluminum hydride, preferably sodium borohydride. Suitable protic solvents for this reaction include alcohols, and preferably ethanol.

Reaction 6 is a standard amino deprotection reaction using procedures and methods well known to those skilled in the art to afford the corresponding amine which may be isolated or further reacted in Reaction 7.

Reaction 7 is a standard coupling reaction commonly employed in the synthesis of peptides where an amine is reacted with a carboxylic acid in an aprotic solvent or mixture of solvents in the presence or absence of a catalyst, preferably in the presence of a catalyst, and in the presence of a coupling reagent. Suitable aprotic solvents for this reaction are tetrahydrofuran and dimethylformamide, and preferably a mixture of such solvents, at a temperature from about −30° C. to about 25° C. A catalyst is preferably included for this reaction and the preferred catalyst is hydroxybenzotriazole. Examples of suitable coupling reagents include the carbodiimides such as N,N¹-diethylcarbodiimide; the imidazoles such as carbonyldiimidazole; as well as reagents such as 1-hydroxybenzotriazole mesylate or N-ethoxycarbonyl-2-ethoxy- 1,2-dihydroquinoline (EEDQ). The coupling reaction is carried out by adding about an equimolar quantity of the amine to a solution of the carboxylic acid in the presence of an equimolar quantity to slight excess of the coupling reagent. The preferred coupling reagent for this reaction is dicyclohexyl carbodiimide. The coupling reaction affords the compounds of Formula I or their precursors.

Alternatively, the divalent $-(NH-CHR^2-C(O))_n-$ moiety can be coupled with the intermediate afforded by Reaction 6 and then coupled to an R—X—COOH to afford compounds of Formula I, where n, R, X and $R_2$ are as defined above for Formula I. In such a case, the reactant $Cb_z-(NH-CHR^2-C(O))_n-$OH is reacted with the intermediate afforded by Reaction 6 under standard coupling reaction conditions well known to those skilled in the art and commonly employed in the synthesis of peptides. The amino protecting group, $CB_z$ is shown and preferred, but others may also be employed, is removed again using standard amino deprotection reaction conditions well known to those skilled in the art to afford the corresonding intermediate having a terminal primary amino reactive group. A further coupling reaction is carried out with the R—X—COOH reactant again under standard coupling reaction conditions well known to those skilled in the art and commonly employed in the synthesis of peptides, to afford the compounds of Formula I.

In addition, for those compounds where X is —N(R⁵)(CH₂—)ₘ—, the amine intermediate may be reacted with compounds of the formula, R—(CH₂—)ₘ—N=C=O to afford compounds of Formula I, where R, m and R⁵ are as defined above for Formula I. The isocyanate reactant, R—(CH₂—)ₘ—N=C=O, to the extent not commercially available, is prepared by standard methodology well known to those skilled in the art. The reaction is carried out by combining an equimolar quantity of the amine intermediate with an equimolar quantity to a slight excess of the isocyanate reactant. The reaction is carried out in an aprotic solvent, at a temperature from about 15° C. to about 35 C, and preferably under an inert atmosphere, such as nitrogen. Suitable aprotic solvents for this reaction are tetrahydrofuran and acetonitrile. The reaction affords compounds of Formula I, wherein X is —N(R⁵)(CH₂—)ₘ—.

The Weinreb Amide used as a reactant in Reaction 4 is prepared by reacting an amino-protected amino acid with N-methoxy-N-methyl-amine in the presence of a catalyst, an acid scavenger, and a coupling agent and preferably in the presence of an emulsifier in an aprotic solvent or mixture of solvents at a temperature of from about −25° C. to 25° C. The preferred catalyst for this reaction is hydroxybenzotriazole. The preferred acid scavenger is a tertiary alkylamine and preferably triethylamine. The preferred emulsifier for this reaction is N-methylmorpholine. The preferred coupling reagent is ethyl dimethylaminopropylcarbodiimide hydrochloride. The Weinreb Amide afforded by this reaction is preferably isolated prior to its use in Reaction 4 of Scheme 1.

The acid reactant in Reaction 7, to the extent not commercially available, is prepared by standard methodology well known to those skilled in the art.

Suitable amino-protecting groups are those substituents of an amino group commonly employed by those skilled in the art to block or to protect the amino functionality while reacting other functional groups on the compound as defined above. Preferred amino-protecting groups are t-butoxycarbonyl (Boc) and benzyloxycarbonyl (cbz).

The compounds of Formula I where R³ is bonded through a nitrogen atom (groups 4 through 6 in the definition of R³) are prepared according to the procedures shown below in Scheme 2 and as described following Scheme 2.

Scheme 2:

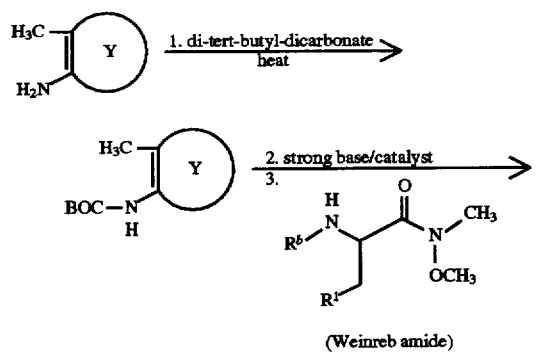

(Weinreb amide)

-continued
Scheme 2:

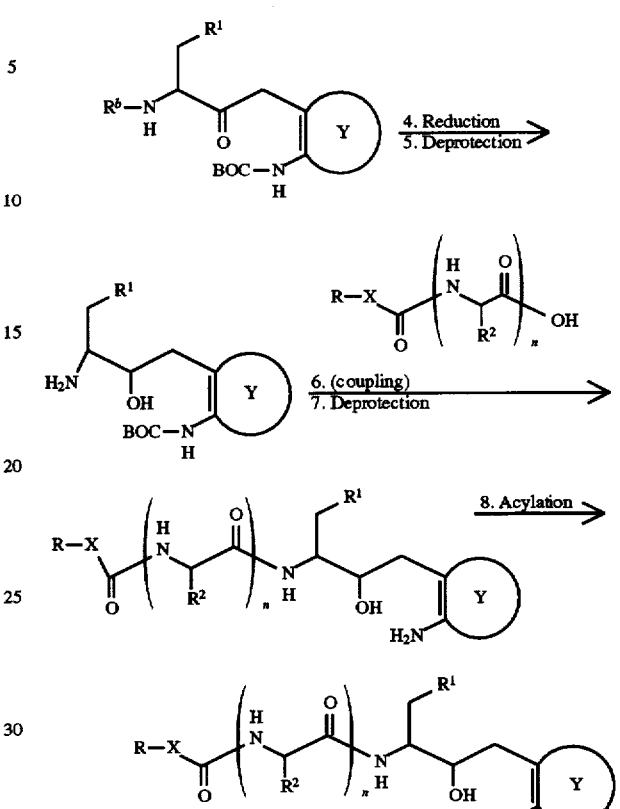

wherein R, X, n, R¹, R² and Y are as defined above for Formula I, Rᵇ is an amino protecting group, and R³ᵇ is group 4 through 6 of R³ as defined above for Formula I.

In Scheme 2, a suitable aryl or unsaturated heterocycle amine is amino-protected, as necessary, in Reaction 1 under standard conditions well known to those skilled in the art. Reactions 2 through 6 are carried out substantially as described above in Scheme 1 for Reactions through 7. In Scheme 2, a further deprotective reaction, Reaction 7, is necessary to remove the amino protecting group introduced in Reaction 1. This is a standard amino deprotection reaction using procedures and methods well known to those skilled in the art. For example, the Boc group illustrated in Reaction 1, Scheme 2, is removed using a strong acid, preferably trifluoroacetic acid. Finally, in Reaction 8, the illustrated intermediate is acylated with a suitable acid chloride, isocyanate or chloroformate, preferably in the presence of an acid scavenger such as triethylamine.

Alternatively, the divalent moiety —(N—H—CHR₂—C(O)—)ₙ portion of the reactant illustrated for Reaction 6 can be coupled to the intermediate afforded by Reaction 5 substantially as described above for Scheme 1, where n and R² are as defined above for Formula I. The coupling reaction with an R—X—COOH reactant, where R and X areas defined above for Formula I, can be carried out prior to or subsequent to the acylation step, Reaction 8. In either instance, deprotection of the primary amine functional group on the corresponding intermediate is required prior to the coupling or acylation reactions. To facilitate deprotection of the desired primary amine, the amino protecting groups employed should not both be removable under substantially similar conditions. Such deprotection is carried out by standard techniques and under standard conditions for such reactions well known to those skilled in the art. As described above for Scheme 1, the coupling reaction with an R—X—COOH is, again, a standard coupling reaction carried out under conditions well known to those skilled in the art and commonly employed in the synthesis of peptides.

As noted above, the optically active diastereomers of the compounds of Formula I are considered part of this invention. Such optically active isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., Enantiomers, Racemates, and Resolutions, john Wiley & Sons 1981.

The compounds employed as initial starting material in the synthesis of the compounds of this invention are well known and, to the extent not commercially available are readily synthesized by standard procedures commonly employed by those of ordinary skill in the art.

The pharmaceutically acceptable salts of the invention are typically formed by reacting a compound of Formula I with an equimolar or excess amount of acid or base. The reactants are generally combined in a mutual solvent such as diethyl ether or benzene, for acid addition salts, or water or alcohols for base addition salts, and the salts normally precipitate out of solution within about one hour to about ten days and can be isolated by filtration or other conventional methods.

In addition some of the compounds of Formula I may form solvates with water or with common organic solvents. Such solvates are included within the scope of the compounds of the present invention.

The following Preparations and Examples further illustrate the compounds of the present invention and methods for the synthesis. The examples are not intended to be limiting to the scope of the invention in any respect and should not be so construed.

Unless otherwise noted, NMR data appearing in the examples refers to the free base of the subject compound.

In the following Preparations and Examples, the terms melting point, nuclear magnetic resonance spectra, electron impact mass spectra, field desorption mass spectra, East atom bombardment mass spectra, infrared spectra, ultraviolet spectra, elemental analysis, specific rotation, high performance liquid chromatography, and thin layer chromatography are abbreviated m.p., n.m.r., m.s., f.d.m.s., f.a.b.m.s., i.r., u.v., anal., o.r., HPLC, and TLC, respectively. In addition, the absorption maxima listed for the i.r. spectra are only those of interest and not all of the maxima observed.

In conjunction with n.m.r. spectra, the following abbreviations are used: "s" is singlet, "d" is doublet, "dd" is doublet of doublets, "t" is triplet, "q" is quartet, "m" is multiplet, "dm" is a doublet of multiplets and "br.s", "br.d", "br.t", and "br.m" are broad singlet, doublet, triplet, and multipier respectively. "J" indicates the coupling constant in Hertz. "DMSO-$d_6$" is dimethyl sulfoxide where protons have been replaced with deuterium.

The n.m.r. spectra were obtained on a Varian Associates EM-390 90 MHz or T-60 60 MHz instrument, on a Jeol FX-90Q 90MHz instrument, on a Brüker Corp. 270 MHz instrument or on a General Electric QE-300 300 MHz instrument. The chemical shifts are expressed in delta values (parts per million downfield from tetramethylsilane). The field desorption mass spectra were taken on a Varion-MAT 731 Spectrometer using carbon dendrite emitters. Electron Impact Mass Spectra were obtained on a CEC 21–110 instrument from Consolidated Electrodynamics Corporation. Infrared spectra were obtained on a Perkin-Elmer 281 instrument. Ultraviolet Spectra were obtained on a Cary 118 instrument. Specific rotations were obtained on a Perkin-Elmer Q-41 instrument. Thin layer chromatography was carried out on E. Merck silica gel plates. Melting points are uncorrected.

PREPARATION 1

Preparation of (S)-N-methoxy-N-methyl-2-(N-phenylmethyloxycarbonyl)amino-3-phenylpropanamide A. 1 L, single necked round bottom flask was charged with 50.35 g (0.17 mol) cbz-L-phenylalanine in 600 mL methylene chloride ($CH_2Cl_2$). To this solution was added 21.3 g (0.22 mol) N,O-dimethylhydroxylamine, 30 mL (22 g, 0.22 mol) triethylamine (TEA), 29.6 g (0.22 mol) 1-hydroxybenztriazole hydrate (HOBT), and 37 mL (34 g, 0.34 mol) N-methylmorpholine. The resulting solution was cooled to 0° C. and 35.5 g (0.19 mol) 1-(3-dimethylaminopropyl)-3-ethylcarbodiimide hydrochloride (EDC) was added in one portion. The reaction mixture was stirred at 0° C. for one hour, and then warmed to room temperature and stirred overnight. The solution was then diluted with 900 mL hexane and transferred to a separatory funnel, where it was washed twice with 500 mL saturated $NaHCO_3$, twice with 500 mL 1M $NaHSO_4$, once with 500 mL brine, and dried over $Na_2SO_4$. Removal of the drying agent by filtration and concentration in vacuo afforded a viscous colorless oil (56.89 g, 97%).

$[a]_D$+11.33° (c 1.059, MeOH).

IR ($CHCl_3$) 3435, 3027, 3013, 1717, 1659, 1507, 1455, 1392, 1231, 1051 $cm^{-1}$.

MS (FD) m/e 342(M+), 342(100).

Analytical calc'd for $C_{19}H_{22}N_2O_4$: C 66.65, H 6.48, N 8.18; found C 66.58, H 6.59, N 8.20.

PREPARATION 2

Preparation of quinaldic acid pentafluorophenyl ester

A. An oven dried single necked round bottom flask was charged with 15.0 g quinaldic acid (86.6 mmol), 20.8 g pentafluorophenol (113 mmol), and 200 mL THF. The suspension was stirred, and 18.3 g EDC (95.3 mmol) was added in one portion. Vigorous stirring was continued at room temperature for two hours, during which time a gummy precipitate formed at the bottom of the flask. The solution was decanted from the gum, and the gum was washed with $CH_2C_{12}$. The combined organic layers were diluted with hexane and washed once with 50 mL 0.1N $NaHSO_4$, twice with 50 mL 1N $K_2CO_3$, and once with 50 mL brine. The organic layer was dried over $Na_2SO_4$, filtered, and concentrated in vacuo, affording a pale pink solid. The solid was dissolved in 30 mL hot diethyl ether and 400 mL hot hexane was added. The solution was allowed to cool to room temperature, and then to 0° C. over a period af 1.5 hours. The desired product was collected as colorless needles (21.6 g, 73%) by filtration.

$^1$H NMR (300 MHz, $CDCl_3$) d 7.73 (t, J=7.5 Hz, 1H), 7.86 (t, J=7.9 Hz, 1H), 7.95 (d, J=8.2 Hz, 1H), 8.29–8.42 (m, 3H).

IR ($CHC_{13}$) 3035, 2997, 1763, 1522, 1285, 1068, 998, 842 $cm^{-1}$.

Analytical calc'd for $C_{16}H_6NO_2F_5$: C 56.65, H 1.78, N 4.13; found C 56.66, H 1.77, N 4.12.

PREPARATION 3

Preparation of (S)-2-(2-N-quinolinylcarboxy)-2,4-diamino-1,4-butanedioic acid

B. A 1L round bottom flask was charged with 17.9 g quinaldic acid pentafluorophenyl ester (51.2 mmol), 6.99 g L-asparagine monohydrate (46.6 mmol), 15.7 g sodium bicarbonate (186 mmol), 265 mL water and 219 mL dioxane. The resulting suspension was stirred vigorously overnight at room temperature, during which time >90% of the reaction mixture was solubilized. The reaction mixture was concentrated in vacuo to remove the dioxane, and the resulting aqueous layer acidified to pH 3 with 2N $NaHSO_4$. The aqueous layer was then extracted three times with 60 mL 3:1 chloroform ($CHCl_3$)/isopropanol (i-PrOH). The combined organic layers were washed once with 50 mL brine and dried over $Na_2SO_4$. Removal of the drying agent by filtration followed by concentration under reduced pressure provided a colorless solid, which was washed with 500 mL diethyl ether and 250 mL hot hexanes to remove residual pentafluorophenol. The remaining solid was dried at 80° C. in a vacuum oven for three hours, giving 10.61 g (79%) of the desired product.

$[a]_D$+16.54° (c 1.01, DMSO).

$^1$H NMR (300 MHz, DMSO-$D_6$) d 2.68 (dd, J=16.0, 4.9 Hz, 1H), 2.81 (dd, J=16.0, 5.7 Hz, 1H), 4.74–4.81 (m, 1H), 6.96 (s, 1H), 7.70 (t, J=7.5 Hz, 1H), 7.85 (t, J=7.5 Hz, 1H), 8.05–8.15 (m, 3H), 8.56 (d, J=8.5 Hz, 1H), 9.12 (d, J=8.6 Hz, 1H), 12.8 (s, 1H).

IR (KBr) 3385, 3367, 3216, 1171, 1662, 1523, 1499, 1427, 780, 592 cm$^{-1}$.

MS (FD) m/e 288 (M+), 288 (100).

Analytical calc'd for $C_{14}H_{13}N_3O_4$: C 58.53, H 4.56, N 14.63; found C 58.80, H 4.57, N 14.56.

EXAMPLE 1

[1S-(1R*, 4R*, 5S*)]-N-(1-(2-amino-2-oxoethyl)-2-oxo-3-aza-4-phenylmethyl-5-hydroxy-6-(2-(1-t-butylamino-1-oxomethyl)phenyl)hexyl)-2-quinolinyl carboxamide

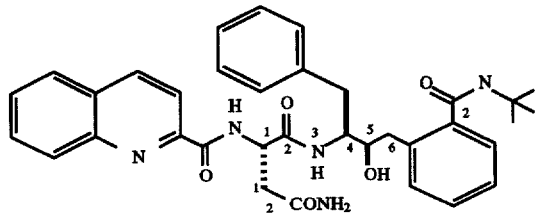

Preparation of N-t-butyl-2-methylbenzamide

A three-necked 3-L round bottom flask fitted with a thermometer, mechanical stirrer and nitrogen inlet was charged with 139.2 g (0.9 moles, 1.0 equiv.) of o-toluoyl chloride in 1200 mL of methylene chloride ($CH_2Cl_2$) at 25° C. under a flow of nitrogen. Upon dissolving, the stirring solution, under a static atmosphere, was cooled to 0° C. with an ice/salt bath and 180.0 g of triethylamine (1.8 moles, 2.0 equiv.), was added dropwise via an addition funnel over a period of 30 minutes. Immediately after adding the triethylamine, a solution of 73.14 g (1.0 mol, 1.1 equiv.) of t-butylamine in methylene chloride (200 mL) was added dropwise over 1.5 h. Upon completion of the addition, the reaction was allowed to warm to room temperature and stir 2.5 h. Next 300 mL of water was added to the reaction mixture, and it was poured into a separatory funnel containing 1500 mL of water. The organic layer was washed with 2×150 mL 2N NaOH, 1×150 mL of 1.0/HCl, and 2×250 mL of brine. The organic layer was dried over magnesium sulfate, filtered, and evaporated under reduced pressure to give 167.6 g (97%) of an off-white solid, mp 77°–78° C.

$^1$H NMR (300 MHz, CDCl$_3$) d 1.41 (s, 9H, —C(CH$_3$)3), 2.41 (s, 3H, ARCH$_3$), 5.54 (br s, 1H, —NE), 7.13–7.30 (m, 4H, aromatics).

IR (CHCl$_3$) 3430, 3011, 2971, 2932, 1661, 1510, 1484, 1452, 1393, 1366, 1304, 1216, 876 cm$^{-1}$.

MS (FD) m/e 191(M+), 191(100).

Analytical calc'd for $C_{12}H_{17}NO$: C 75.35, H 8.76, N 7.32; found C 75.10, H 9.11, N 7.20.

Preparation of (S)-N-C-butyl-2-(3-(N-phenylmethoxycarbonyl)amino-3-phenylmethyl-2-oxopropyl)benzamide A solution of 7.0 g (36.5 mmol) N-t-butyl-2-methylbenzamide in 200 mL anhydrous tetrahydrofuran (THF) was prepared under a nitrogen atmosphere in an oven dried, 500 mL pear shaped flask fitted with a rubber septum. To this solution, 12.1 mL (9.3 g, 80.3 mmol, 2.2 equiv.) N,N,N',N'-tetramethylethylenediamine (TMEDA) was added via syringe. The solution was cooled to −78° C., and 55.9 mL sec-butyllithium was added dropwise through a syringe at a rate such that the internal temperature of the reaction did not go above −60° C. The dianion solution was allowed to stir for 1 hr. at −78° C., and then a solution of 5.00 g (14.6 mmol) (S)-N-methoxy-N-methyl-2-(N-phenylmethyl-oxycarbonyl)amino-3-phenylpropanamide in 50 mL anhydrous THF (prepared in a separate oven dried 100 mL round bottom flask under nitrogen atmosphere) was added via cannula while keeping the reaction temperature below −65° C. When the addition was complete, the reaction mixture was allowed to warm to −20° C. and quenched with 20 mL saturated NH$_4$Cl. The reaction mixture was then diluted with 200 mL diethyl ether (Et$_2$O) and transferred to a separatory funnel, where the layers were separated. The organic layer was washed twice with 200 mL H$_2$O, once with 200 mL 0.2N NaHSO$_4$, once with 150 mL brine, and then dried over Na$_2$SO$_4$. Removal of the drying agent by filtration followed by concentration in vacuo gave a colorless oil which was purified by flash chromatography with 3:1 CH$_2$Cl$_2$/ethyl acetate (EtOAc). The product was isolated as a colorless foam (6.08 g, 88%).

$[a]_D$−289.26° (c 0.12, MeOH).

$^1$H NMR (300 MHz, CDCl$_3$) d 1.38 (s, 9H, —C(CH$_3$)$_3$), 2.99 (dd, J=15, 6 Hz, 1H), 3.24 (dd, J=15, 6 Hz, 1H), 3.89 (d, J=18 Hz, 1H), 4.16 (d, J=18 Hz, 1H), 4.72 (dd, J=15, 6 Hz, 1H), 5.00–5.09 (m, 2H), 5.56 (d, J=6 Hz, 1H), 5.93 (br s, 1H), 7.03–7.40 (m, 14H, aromatics).

IR (CHCl$_3$) 3431, 3027, 3012, 2973, 1713, 1658, 1511, 1454, 1383, 1366, 1307, 1231, 1046 cm$^{-1}$.

MS (FD) m/e 472(M$^+$), 218(100).

Analytical calc'd for $C_{29}H_{32}N_2O_4$: C 73.70, H 6.82, N 5.93; found C 73.41, H 6.98, N 5.83.

Preparation of [R-(R*, S*)]-N-t-butyl-2-(3-(N-phenylmethoxycarbonyl)amino-3-phenylmethyl-2-hydroxypropyl)benzamide A solution of 6.96 g (14.7 mmol) (S)-N-t-butyl-2-(3-(N-phenylmethoxycarbonyl)amino-3-phenylmethyl-2- oxopropyl)benzamide in 200 mL absolute ethanol was prepared in a 500 mL round bottom flask under a nitrogen atmosphere. To this solution was added in one portion 2.78 g NaBH$_4$ (73.5 mmol). There was an initial slight exotherm, and the mixture quickly cooled back to room temperature. The solution was allowed to stir at room temperature, and was monitored by tlc. After four hours, the reaction was complete. The ethanol solution was diluted with 200 mL EtOAc, and quenched by dropwise addition of 20 mL saturated NH$_4$Cl. The organic layer was then washed once with 150 mL 1N HCl, once with 100 mL saturated NaHCO$_3$, and once with 100 mL brine. Drying over Na$_2$SO$_4$ followed by filtration and concentration under reduced pressure afforded a colorless oil (6.4 g, 93%) that was determined to be a 9:1 mixture of diastereomers by $^1$H NMR. The major, desired diastereomer was isolated by flash chromatography with a gradient of 49:1 to 9:1 ethyl acetate/CH$_2$Cl$_2$ (5.12 g, 74%).

[a]$_D$+10.38° (c 0.10, MeOH).

$^1$H NMR (300 MHz, CDCl$_3$) d 1.40 (s, 9H, —C(CH$_3$)$_3$), 2.79 (dd, J=12, 3 Hz, 1H), 2.90–2.98 (m, 2H), 3.04 (44, J=12, 3 Hz, 1H), 3.70–3.81 (m, 1H), 3.97 (m, 1H), 4.96–5.08 (m, 2H), 5.10 (d, J=9 Hz, 1H), 5.88 (d, J=6 Hz, 1H), 5.93 (s, 1H), 7.13–7.42(m, 14H).

IR (CHCl$_3$) 3431, 3028, 3012, 2971, 1773, 1643, 1515, 1454, 1367, 1229, 1028 cm$^{-1}$.

MS (FD) m/e 475 (M$^+$), 475 (100).

Analytical calc'd for C$_{29}$H$_{34}$N$_2$O$_4$: C 73.39, H 7.22, N 5.99; found C 73.12, H 7.48, N 5.62.

Preparation of [R-(R*, S*)]-N-C-butyl-2-(3-amino-2-hydroxypropyl)benzamide

A solution of 41.0 g of the [R-(R*, S*)]-N-t-butyl-2-(3-(N-phenylmethoxycarbonyl)amino-3-phenylmethyl-2-hydroxypropyl)benzamide (120 mmol) in 150 mL absolute ethanol was prepared and subjected to hydrogenation over 10% Pd/C (500 mg) in a Parr shaker apparatus. The catalyst was removed by filtration, and the filtrate concentrated in vacuo to give 31.1 g (96%) of a light yellow foam. The foam was coupled without further purification to (S)-2-(2-N-quinolinylcarboxy)-2,4-diamino-1,4-butanedioic acid.

[a]$_D$+34.68° (c 1.0, MeOH).

$^1$H NMR (300 MHz, CDCl$_3$) d 1.46 (s, 9H), 2.71 (dd, J=13.7, 9.5 Hz, 1H), 2.84 (dd, J=13.3, 2.51 Hz, 1H), 2.95–3.06 (m, 2H), 3.23–3.29 (m, 1H), 3.84–3.90 (m, 1H), 6.23 (s, 1H), 7.19–7.37 (m, 12H).

IR (CHCl$_3$) 3440, 3382, 3007, 2970, 2934, 1643, 1516, 1454, 1367, 1213 cm$^{-1}$.

MS (FD) m/e 341(M$^+$), 341(100).

Preparation of [1S-(1R*, 4R*, 5S*)]-N-(1-(2-amino-2-oxoethyl)-2-oxo-3-aza-4-phenylmethyl-5-hydroxy-6-(2-(1-t-butylamino-1-oxomethyl)phenyl) hexyl)-2-quinolinyl carboxamide A solution of 500 mg [R-(R*, S*)]-N-C-butyl-2-(3-amino-2-hydroxypropyl)benzamide (1.46 mmol) in 10 mL anhydrous THF was prepared in a single necked 50 mL round bottom flask. To this was added 443 mg (S)-2-(2-N-quinolinylcarboxy)-2,4-diamino-1,4-butanedioic acid (1.54 mmol), 208 mg HOBT·H$_2$O (1.54 mmol), and 1.75 mL anhydrous DMF (enough to obtain a homogeneous solution). The solution was cooled to −10° C. in an ice/acetone bath, and 309 mg dicyclohexylcarbodiimide (DCC) (1.50 mmol) was added in one portion. The mixture was stirred under N$_2$ at −10° C. for 20 minutes, and then at 0° C. for 1 hour. The stirring solution was then allowed to warm to room temperature and stir overnight, during which time the dicyclohexylurea precipitate began to form. After stirring overnight, the reaction mixture was cooled to 0° C. and filtered to remove the precipitate. The filtrate was concentrated in vacuo, and the residue taken up in 50 mL ethyl acetate. The ethyl acetate solution was washed once with 20 mL water, once with 15 mL saturated NaHCO$_3$. once with 15 mL 5% citric acid, and once with 20 mL brine. The organic layer was dried over Na$_2$SO$_4$, filtered and concentrated under reduced pressure. The resulting foam was purified by radial chromatography (1.0 mm plate, 0–10% MeOH/CH$_2$Cl$_2$ gradient), affording 487 mg (55%) of the desired product as a single diastereomer as determined by 300 MHz 1H NMR.

[a]$_D$+11.93° (c 0.10, MeOH)

$^1$H NMR (300 MHz, CDCL$_3$) d 1.46 (s, 9H, —C(CH$_3$)$_3$), 2.71 (dd, J=15, 6 Hz, 1H), 2.81–3.01 (m, 4H), 3.07 (dd, J=15, 3 Hz, 1H), 3.75–3.78 (m, 1H), 4.28–4.32 (m, 1H), 4.95 (dd, J=12, 6 Hz, 1H), 5.74 (br s, 1H), 6.19 (br s, 1H), 6.32 (br.s, 1H), 6.90 (t, J=6 Hz, 1H), 7,01 (t, J=6 Hz, 1H), 7.08–7.38 (m, 6H), 7.64 (t, J=6 Hz, 1H), 7.79 (t, J=9 Hz, 1H), 7.80 (d, J=6 Hz, 1H), 8.17–8.31 (m, 3H), 9.22 (d, J=9 Hz, 1H).

$^{13}$C NMR (75.4 MHz, CDCl$_3$) d 28.7, 35.3, 37.1, 37.2, 50.1, 52.1, 53.5, 55.9, 74.8, 118.7, 126.0, 127.0, 127.6, 128.2, 129.3,129.4, 130.0, 130.2, 130.3, 130.9, 137.4, 137.5, 138.2, 146.5, 148.8, 164.6, 170.4, 170.5.

IR (CHCl$_3$) 3428, 3411, 3359, 30 12, 2975, 1681, 160 1, 1565, 1518, 1499, 1454, 1428, 1395, 1367, 1231, 1047 cm$^{-1}$.

MS (FD) m/e 610 (M+), 221(100).

Analytical calc'd for C$_{35}$H$_{39}$N$_5$O$_5$: C 68.95, H 6.45, N 11.49; found C 68.76, H 6.55, N 11.49.

EXAMPLE 2

[1S-(1R*, 4R*, 5S*)]-N-(1-(2-amino-2-oxoethyl)-2-oxo-3-aza-4-phenylmethyl-5-hydroxy-6-(2-(1-t-butylamino-1-oxomethyl)-4-methylphenyl)hexyl)-2-quinolinyl carboxamide Preparation of N-t-butyl-2,5-dimethylbenzamide The title compound was prepared according to the procedure in Example 1. Recrystallization from hexane/ethyl acetate afforded 67.2 g of the desired product (67%), mp 80°–82° C.

$^1$H NMR (300 MHz, CDCl$_3$) d 1.44 (s, 9H, —C(CH$_3$)$_3$), 2.29 (s, 3H), 2.36 (s, 3H), 5.58–5.46 (br.s, 1H), 7.06 (s, 2H), 7.10 (s, 1H)

IR (CHCl$_3$) 3430, 3009, 2970, 2928, 2871, 1662, 1551, 1453, 1355, 1236 cm$^{-1}$.

MS (FD) m/e 205(M+), 205(100).

Analytical calc'd for C$_{13}$H$_{19}$NO: C 76.05, H 9.33, N 6.82; found C 76.30, H 9.60, N 6.83.

Preparation of (S)-N-C-butyl-2-(3-(N-phenylmethoxycarbonyl)amino-3-phenylmethyl-2-oxopropyl)-5-methylbenzamide The title compound was prepared according to the procedure outlined in Example 1. Flash chromatography with 20–50% ethyl acetate/hexane provided 6.31 g of the product ketone (89%) as a crystalline solid.

[a]$_D$−25.74° (c 0.30, MeOH).

$^1$H NMR (300 MHz, CDCl$_3$) d 1.38 (s, 9H), 2.32 (s, 3H), 2.98 (dd, H =14, 8 Hz, 1H), 3.22 (dd, J=14, 5 Hz, 1H), 3.93

(d, J=18 Hz, 1H), 4.10 (d, J=18 Hz, 1H), 4.65–4.76 (m, 1H), 5.00–5.10 (m, 2H), 5.58 (d, J=6.7 Hz, 1H), 5.94 (s, 1H), 6.92 (d, J=8Hz, 1H), 7.09–7.39 (m, 12H).

IR (CHCl$_3$) 3481, 3029, 3012, 2972, 1713, 1656, 1496, 1454, 1236, 1045 cm$^{-1}$.

MS (FD) m/e 486(M+), 486(100).

Analytical calc'd for C$_{30}$H$_{34}$N$_2$O$_4$: C 74.05, H 7.04, N 5.76; found C 73.99, H 7.28, N 5.65.

Preparation of [R-(R*, S*)]-N-t-butyl-2-(3-(N-phenyl-methoxy-carbonyl)amino-3-phenylmethyl-2-hydroxypropyl)-5-methylbenzamide The title compound was prepared according to the procedure in Example 1. Flash chromatography with 2–50% ethyl acetate/hexane afforded the desired alcohol (4.84 mg, 82%) as a colorless foam.

[a]$_D$+10.31° (c 0.58, MeOH) .

$^1$H NMR (300 MHz, CDCl$_3$) d 1.46 (s, 9H), 2.32 (s, 3H), 2.76 (d, J=15 Hz, 1H), 2.85–2.95 (m, 2H), 3.04 (dd, J=15, 5 Hz, 1H), 3.67–3.74 (m, 1H), 3.92–4.05 (m, 1H), 4.92–5.14 (m, 3H), 5.86 (d, J=7 Hz, 1H), 5.91 (s, 1H), 7.03–7.40 (m, 13H).

IR (CHCl$_3$) 3431, 3274, 3027, 3012, 2970, 1713, 1643, 1514, 1496, 1454, 1367, 1224, 1039, 910 cm$^{-1}$.

MS (FD) m/e 489 (M$^+$), 205 (100).

Analytical calc'd for C$_{30}$H$_{36}$N$_2$O$_4$: C 73.74, H 7.43, N 5.73; found C 73.55, H 7.50, N 5.96.

Preparation of [R-(R*, S*)]-N-t-butyl-2-(3-amino-2-hydroxypropyl)-5-methylbenzamide The title compound was prepared according to the procedure given in Example 1. Concentration of the crude filtrate afforded the amino alcohol (4.2 g, 89%) as a colorless foam that was carried on directly to the next step without any further purification.

Preparation of [1S-(1R*, 4R*, 5S*)]-N-(1-(2-amino-2-oxoethyl)-2-oxo-3-aza-4-phenylmethyl-5-hydroxy-6-(2-(1-t-butylamino-1-oxomethyl)-4-methylphenyl)hexyl)-2-quinolinyl carboxamide The title compound was prepared as described in Example 1. Flash chromatography with 2–8% MeOH/CH$_2$Cl$_2$ provided 2.00 g (80%) of the desired product (>90% purity as determined by $^1$H NMR). Further purification of the product by reverse phase preparatory chromatography provided 1.95 g (74%) of analytically pure material.

[a]$_D$+28.57° (c 0.10, MeOH).

$^1$H NMR (300 MHz, CDCl$_3$) d 1.43 (s, 9H), 2.30 (s, 3H), 2.63–3.05 (m, 6H), 3.65–3.76 (m, 1H), 4.22–4.35 (m, 1H), 4.89–4.97(m, 1H), 5.51 (s, 1H), 5.82–5.88 (br.s, 1H), 6.09 (s, 1H), 6.20 (s, 1H), 6.84–7.24 (m, 10H), 7.63 (t, J=7.5 Hz, 1H), 7.78 (t, J=7.5 Hz, 1H), 7.85 (d, J=8 Hz, 1H), 8.19 (t, J=8.4 Hz, 1H), 8.28 (d, J=8.4 Hz, 1H), 9.20 (d, J=8.1 Hz, 1H).

IR (CHC13) 3410, 3022, 3013, 1674, 1519, 1497, 1454, 1428, 1367, 1210, 1047, 910 cm$^{-1}$.

MS (FD) m/e 624 (M$^+$), 234 (100).

Analytical calc'd for C$_{36}$H$_{41}$N$_5$O$_5$: C 69.32, H 6.63, N 11.23; found C 68.73, H 6.76, N 11.07.

EXAMPLE 3

[1S-(1R*, 4R*, 5S*)]-N-(1-(2-amino-2-oxoethyl)-2-oxo-3-aza-4-phenylmethyl-5-hydroxy-6-(2-(1-t-butylamino-1-oxomethyl)-3-methylphenyl)hexyl)-2-quinolinyl carboxamide Preparation of N-t-butyl-2,6-dimethylbenzamide The title compound was prepared according to the procedure in Example 1. Recrystallization from hexane/ethyl acetate afforded 42.3 g of the desired product (75%), mp 134°–136° C.

$^1$H NMR (300 MHz, CDCl$_3$) d 1.45 (s, 9H, —C(CH$_3$)$_3$), 2.32 (s, 6H, 2 x o-CH$_3$), , 5.45(br.s, 1H, -NH), 6.98 (d, J=6 Hz, 2H, m-ArH), 7.12 (t, J=9Hz, 1H, p-ArH).

IR (CHCl$_3$) 3426, 3009, 2970, 2929, 1663, 1508, 1452, 1360, 1213 cm$^{-1}$.

MS (FD) m/e 205(M+), 205(100).

Analytical calc'd for C$_{13}$H$_{19}$NO: C 76.05, H 9.33, N 6.82; found C 76.35, H 9.53, N 6.80.

Preparation of (S)-N-t-butyl-2-(3-(N-phenylmethoxycarbonyl)amino-3-phenylmethyl-2-oxopropyl)-6-methylbenzamide The title compound was prepared according to the procedure outlined in Example 1. Flash chromatography with 10–100% ethyl acetate/hexane provided 2.28 g of the product ketone (80%) as a colorless foam.

[a]$_D$ –17.00° (c 0.10, MeOH).

$^1$H NMR (300 MHz, CDCl$_3$) d 1.37 (2, 9H, t-Bu), 2.33 (s, 3H, o-Me), 2.98 (dd, J=15, 6 Hz, 1H, PhCH$_2$CH), 3.15 (dd, 15, 6 Hz, 1H, PhCH$_2$CH), 3.73 (d, J=15 Hz, 1H, ArCH$_2$CO), 3.84 (d, J=15 Hz, 1H, ArCH$_2$CO), 4.70 (dd, J=15,6 Hz, 1H ArCH$_2$CH), 4.98–5.02 (m, 2H, PhCH$_2$O), 5.45 (d, J=9 Hz, 1H, —NHCH), 5.94 (s, 1H, —NHt-Bu), 6.81 (d, J=6 Hz, 1H), 7.06–7.31 (m, 12H, ArH).

IR (CHCl$_3$) 3423, 3030, 3012, 2968, 1713, 1659, 1507, 1455, 1393, 1367, 1305, 1229, 1218, 1045 cm$^{-1}$.

MS (FD) m/e 487(M+), 337(100).

Analytical calc'd for C$_{30}$H$_{34}$N$_2$O$_4$: C 74.05, H 7.04, N 5.76; found C 72.44, H 6.82, N 5.54.

Preparation of [R-(R*, S*)-N-t-butyl-2-(3-(N-phenylmethoxycarbonyl)amino-3-phenylmethyl-2-hydroxypropyl)-6-methylbenzamide The title compound was prepared according to the procedure in Example 1. Flash chromatography with 2–50% EtOAC/CH$_2$Cl$_2$ afforded the desired alcohol (852 mg, 85%) as a colorless foam.

[a]$_D$–4.95° (c 0.10, MeOH)

$^1$H NMR (300 MHz, CDCl$_3$) d 1.45 (s, 9H, t-Bu), 2.35 (s, 3H, o-CH$_3$), 2.68–2.94 (m, 4H, ArCH$_2$CO, PhCH$_2$CH), 3.76–3.82 (m, 1H), 3.92–4.04 (m, 1H), 4.93–5.03 (m, 2H, PhCH$_2$O), 5.20 (d, J=6 Hz, 1H, —NH or OH), 5.85 (s, 1H), 7.04 (d, J=6 Hz, 1H), 7.19–7.31 (m, 13H, ArH).

IR (CHCl$_3$) 3424, 3012, 2967, 1714, 1642, 1512, 1454, 1230, 1028 910 cm$^{-1}$.

MS (FD) m/e 489 (M$^+$), 489 (100).

Analytical calc'd for C$_{30}$H$_{36}$N$_2$O$_4$: C 73.74, H 7.43, N 5.73; found C 74.02, H 7.57, N 5.79.

Preparation of [R-(R*, S*)]-N-t-butyl-2-(3-amino-2-hydroxypropyl)-6-methylbenzamide The title compound was prepared according to the procedure given in Example 1. Concentration of the crude filtrate afforded the amino alcohol (282 mg, 82%) as a colorless foam that was carried on directly to the next step without any further purification.

Preparation of [1S-(1R*, 4R*, 5S*)]-N-(1-(2-amino-2-oxoethyl)-2-oxo-3-aza-4-phenylmethyl-5-hydroxy-6-(2-(1-t-butylamino-1-oxomethyl)-3-methylphenyl)hexyl)-2-quinolinyl carboxamide The title compound was prepared as described in Example 1. Flash chromatography with 3% MeOH/CH$_2$Cl$_2$ provided 122 mg (24%) of the desired product (>95% purity as determined by $^1$H NMR).

[a]$_D$+7.38° (c 0.054, MeOH).

$^1$H NMR (300 MHz, CDCl$_3$) d 1.44 (s, 9H, t-Bu), 2.32 (s, 3H, o-CH$_3$ ), 2.64–2.96 (m, 3H, PhCH$_2$CH and ArCHCO), 3.00 (dd, J=9, 6 Hz, 1H, PhCH$_2$CH), 3.73–3.85 (m, 1H), 4.15–4.28 (m, 1H), 4.83–4.97 (m, 1H), 5.62 (s, 1H), 6.10 (s, 1H), 6.29 (s, 1H), 6.86–7.25 (m, 7H, ArH), 7.62 (t, J=6 Hz, 1H), 7.77 (t, J=6 Hz, 1H), 7.86 (d, J=9 Hz, 1H), 8.13–8.29 (m, 2H), 9.14 (d, J=6 Hz, 1H).

IR (CHCl$_3$) 3413, 3017, 1681,1595, 1520, 1500, 1455, 1428, 1368, 1209, 910 cm$^{-1}$.

MS (FD) m/e 624 (M$^+$), 624 (100).

Analytical calc'd for C$_{36}$H$_{41}$N$_5$O$_5$: C 69.32, H 6.63, N 11.23; found C 68.73, H 6.76, N 11.07.

EXAMPLE 4

[1S-(1R*, 4R*, 5S*)]-N-(1-(2-amino-2-oxoethyl)-2-oxo-3-aza-4-phenylmethyl-5-hydroxy-6-(1-(1-t-butylamino-1-oxomethyl)-2-naphthyl)hexyl)-2-quinolinyl carboxamide Preparation of N-t-butyl-2-methyl-1-naphthylamide The title compound was prepared according to the procedure given in Example 1. Recrystallization from hexane/ethyl acetate afforded 20.99 g (68%) of the desired amide as colorless needles, mp 124°–126° C. NMR (300 MHz, CDCl$_3$) d 1.54 (s, 9H, t-Bu), 2.50 (s, 3H), 5.50–5.65 (br.s, 1H), 7.23–7.54 (m, 3H), 7.74 (d, J=10 Hz, 1H), 7.78 (d, J=10 Hz, 1H), 7.87 (d, J=10 Hz, 1H).

IR (CHCl$_3$) 3424, 3010, 2969, 1660, 1512, 1503, 1454, 1366, 1291, 1263, 1221 cm$^{-1}$.

MS (FD) m/e 241(M$^+$), 241(100).

Analytical calc'd for C$_{16}$H$_{19}$NO: C 79.63, H 7.94, N 5.80; found C 79.90, H 8.11, N 5.76.

Preparation of (S)-N-t-butyl-2-(3-(N-phenylmethoxycarbonyl)amino-3-phenylmethyl-2-oxopropyl)-1-naphthylamide The title compound was prepared according to the procedure in Example 1. Flash chromatography with 10–30% ethyl acetate/hexane provided 7.43 g (86%) of the desired ketone as a colorless foam.

[a]$_D$ –6.86° (c 0.10, MeOH).

NMR (300 MHz, CDCl$_3$) d 1.45 (s, 9H, t-Bu), 3.03 (dd, J=15, 8 Hz, 1H), 3.18 (dd, J=15, 5 Hz, 1H), 3.91 (d, J=16 Hz, 1H), 4.04 (d, J=16 Hz, 1H), 4.70–4.80 (m, 1H), 4.94–5.06 (m, 2H), 5.41 (d, J=8 Hz, 1H), 6.12–6.20 (br.s, 1H), 7.10–7.38 (m, 11H), 7.42–7.58 (m, 2H), 7.76–7.85 (m, 2H), 7.93 (s, J=9 Hz, 1H).

IR (CHCl$_3$) 3420, 3029, 3012, 2970, 1713, 1658, 1505, 1455, 1367, 1232, 1045 cm$^{-1}$.

MS (FD) m/e 522(M$^+$), 522(100).

Analytical calc'd for C$_{33}$H$_{34}$N$_2$O$_4$: C 75.84, H 6.56, N 5.36; found C 75.56, H 6.74, N 5.17.

Preparation of [R-(R*, S*)]-N-t-butyl-2-(3-(N-phenylmethoxycarbonyl)amino-3-phenylmethyl-2-hydroxypropyl)-1-naphthylamide The title compound was prepared according to the procedure in Example 1. Flash chromatography with 2–10% ethyl acetate/dichloromethane provided 5.50 g (74%) of the desired alcohol diastereoisomer as a colorless foam.

[a]$_D$+11.85° (c 0.20, MeOH).

$^1$H NMR (300 MHz, CDCl$_3$) d 1.54 (s, 9H, t-Bu), 2.85–3.15 (m, 4H), 3.85–3.95 (m, 1H), 4.00–4.13 (m, 2H), 4.90–5.34 (m, 3H), 5.85–5.95 (m, 1H), 7.05–7.60 (m, 15H), 7.81 (d, J=9 Hz, 2H), 7.91 (d, 9 Hz, 2H).

IR (CHCl$_3$) 3420, 3012, 2970, 1713, 1643, 1515, 1454, 1367, 1219, 1209, 1028 cm$^{-1}$.

MS (FD) m/e 524(M+), 524(100).

Analytical calc'd for C$_{33}$H$_{36}$N$_2$O$_4$: C 75.55, H 6.92, N 5.34; found C 75.41, H 7.16, N 5.14.

Preparation of [R-(R*, S*)]-N-t-butyl-2-(3-amino-2-hydroxypropyl)-1-naphthylamide The title compound was prepared according to the procedure given in Example 1. Concentration of the crude filtrate afforded the amino alcohol (1.30 g, 92%) as a colorless foam that was carried on directly to the next step without any further purification.

Preparation of [1S-(1R*, 4R*, 5S*)]-N-(1-(2-amino-2-oxoethyl)-2-oxo-3-aza-4-phenylmethyl-5-hydroxy-6-(1-(1-t-butylamino-1-oxomethyl)-2-naphthyl)hexyl)-2-quinolinyl carboxamide The title compound was prepared as described in Example 1. Flash chromatography with 2–5% MeOH/CH$_2$Cl$_2$ provided 1.75 g (80%) of the desired product (>90% purity as determined by $^1$H NMR). Further purification of the product by reverse phase preparatory chromatography provided 1.06 g (48%) of analytically pure material.

[a]$_D$+18.82° (c 0.15, MeOH).

$^1$H NMR (300 MHz, CDCl$_3$) d 1.46 (s, 9H), 2.42–2.80 (m, 4H), 3.00 (br.d, J=13.5 Hz, 2H), 3.60–3.93 (m, 2H (rotamers)), 4.65–4.75 (m, 1H), 5.05 (br.s, 0.4H), 5.38 (br.s, 0.6 H), 6.85–6.93 (m, 2H), 7.04 (t, J=7.5 Hz, 2H), 7.18 (d, J=7.4 Hz, 2H), 7.30–7.54 (m, 4H), 7.70 (t, J=7.5 Hz, 1 H), 7.78–7.90 (m, 3H), 7.95–8.12 (m, 3H), 8.17 (d, J=8.5 Hz, 1H), 8.56 (d, J=8.5 Hz, 1H), 8.84 (d, J=7.6 Hz, 1H).

IR (CHCl$_3$) 3414, 3010, 1680, 1519, 1499, 1454, 1428, 1367, 213, 846 cm$^{-1}$.

MS (FD) m/e 660 (M$^+$), 660 (100).

EXAMPLE 5

1S-(1R*, 4R*, 5S*)]-N-(1-(2-amino-2-oxoethyl)-2-oxo-3-aza-4-phenylmethyl-5-hydroxy-6-(3-(1-t-butylamino-1-oxomethyl)-2-naphthyl)hexyl)-2-quinolinyl carboxamide Preparation of N-t-butyl-3-methyl-2-naphthylamide The title compound was prepared according to the procedure given in Example 1. Recrystallization from hexanes afforded 6.80 g (80%) of the desired product, mp 95°–96° C.

$^1$H NMR (300 MHz, CDCl$_3$) d 1.50 (s, 9H), 2.56 (s, 3H), 5.70 (br.s, 1H), 7.40–7.5 (m, 2H), 7.62 (s,: 1H), 7.72–7.80 (m, 3H).

IR (CHCl$_3$) 3430, 3011, 2970, 1666, 1512, 1496, 1452, 1366, 212, 884 cm$^{-1}$.

MS (FD) m/e 241(M$^+$), 241 (100).

Analytical calc'd for C$_{16}$H$_{19}$NO: C 79.63, H 7.94, N 5.80; found C 79.57, H 8.19, N 5.71.

Preparation of (S)-N-t-butyl-3-(3-(N-phenylmethoxycarbonyl)amino-3-phenylmethyl-2-oxopropyl)-2-naphthylamide The title compound was prepared according to the general procedure given in Example 1. Flash chromatography with 3:1 hexanes/ethyl acetate gave 3.41 g (79%) of the desired product as a colorless oil.

[a]$_D$ −32.10° (c 1.028, MeOH).

$^1$H NMR (300 MHz, CDCl$_3$) d 1.43 (s, 9H), 3.01 (dd, J=13.8, 7.3 Hz, 1H), 3.27 (dd, J=14.90, 6.03 Hz, 1H), 4.06 (d, J=18.3 Hz, 1H), 4.34 (d, J=17.4 Hz, 1H), 4.72–4.79 (m, $^1$H), 4.98–5.09 (m, 1H), 5.59 (br.d, J=7.8 Hz, 1H), 6.02 (s, 1H), 7.19–7.35 (m, 10H), 7.48–7.51 (m, 3H), 7.75 (d, J=8.15 Hz, 1H), 7.81 (d, J=8.9 Hz, 1H), 7.87 (s, 1H).

IR (CHCl$_3$) 3400, 3011, 2970, 1713, 1657, 1512, 1454, 1301, 1234, 1105 cm$^{-1}$.

MS (FD) m/e 523(M+), 523(100).

Analytical calc'd for C$_{33}$H$_{34}$N$_2$O$_4$: C 75.84, H 6.56, N 5.36; found C 75.75, H 6.57, N 5.33.

Preparation of[R-(R*, S*)]-N-t-butyl-3-(3-(N-phenylmethoxycarbonyl)amino-3-phenylmethyl-2-hydroxypropyl)-2-naphthylamide The title compound was prepared according to the procedure outlined in Example 1. Flash chromatography with 19:1 hexanes/ethyl acetate afforded 1.87 g (59%) of the desired compound as a colorless foam.

[a]$_D$+11.02° (c 0.998, MeOH).

$^1$H NMR (300 MHz, CDCl$_3$) d 1.53 (s, 9H), 2.93–3.04 (br.m, 5H), 3.85–3.89 (m, 1H), 4.07–4.12 (m, 1H), 5.00–5.10 (m, 2H), 5.16 (d, J=8.8 Hz, 1H), 6.19 (s, 1H), 7.22–7.40 (m, 10H), 7.48–7.56 (m, 2H), 7.74–7.87 (m, 4H).

IR (CHCl$_3$) 3431, 3027, 3011, 1713, 1645, 1514, 1454, 1367, 1223, 1044 cm$^{-1}$.

MS (FD) m/e 524 (M$^+$), 270 (100).

Preparation of [1S-(1R*, 4R*, 5S*)]-N-(1-(2-amino-2-oxoethyl)-2-oxo-3-aza-4-phenylmethyl-5-hydroxy-6-(3-(1-t-butylamino-1-oxomethyl)-2-naphthyl)hexyl)-2-quinolinyl carboxamide The title compound was prepared according to the general procedure in Example 1. Radial chromatography (1 mm silica plate, 0–10% MeOH/CH$_2$C$_{12}$) afforded 162 mg of the product (74%) as a colorless foam.

[a]$_D$+22.83° (c 0.876, MeOH).

$^1$H NMR (300 MHz, CDCl$_3$) d 1.52 (s, 9H), 2.74 (dd, J=15.1, 8.3 Hz, 1H), 2.90–2.98 (m, 3H), 3.10 (apparent dd, J=14.8, 9.8 Hz, 3H), 3.83–3.85 (m, 1H), 4.35–4.38 (m, 1H), 4.96–5.01 m, 1H), 5.47 (s, 1H), 6.09 (s, 1H) 6.22 (s, 1H), 6.91–6.94 (m, 1H), 7.02 (7, J=7.6 Hz, 2H), 7.08–7.13 (m, 1H), 7.22–7.27 ° (m, 3H), 7.44–7.53 (m, 2H), 7.68 (t, J=7.5 Hz, 1H), 7.77–7.86 (m, 4H), 7.92 (d, J=8.0 Hz, 1H), 8.26 (d, J=8.4 Hz, 2H), 8.36 (d, J=8.5 Hz, 1H), 9.32 (d, J=8.2 Hz, 1H).

IR (KBr pellet) 3319, 1659, 1522, 1497, 1427, 1220, 911, 846, 733, 477 cm$^{-1}$.

MS (FD) m/e 661 (M$^+$), 661 (100).

Analytical calc'd for C$_{39}$H$_{41}$N$_5$O$_5$: C 71.00, H 6.26, N 10.61; found C 71.24, H 6.15, N 10.51.

By following the procedures described in Example 1 and employing the appropriate reactants, the compounds of Examples 6 through 27 were prepared.

EXAMPLE 6

[1S-(1R*, 4R*, 5R*)]-N-(1-(2-amino-oxoethyl)-2-oxo-3-aza-4-phenylmethyl-5-hydroxy-6-(2-(1-t-butylamino-1-oxomethyl)phenyl)hexyl)-2-quinolinyl carboxamide The title compound was isolated in 36% yield. $^1$H NMR (300 MHz, CDCl$_3$) d 1.41 (s, 9H), 2.69–3.07 (m, 7H), 3.77–3.84 (m, 1H), 4.23–4.34 (m, 1H), 4.91–5.03 (m, 1H), 5.52–5.62 (m, 1H), 5.98 (s, 1H), 6.32 (br.s, 1H), 7.00 (d, H=8Hz, 1H), 7.06–7.34 (m, 9H), 7.62 (t, J=7.5 Hz, 1H), 7.77 (t, J=7.5 Hz, 1H), 7.87 (d, J=7.5 Hz, 1H), 8.17–8.32 (m, 3H), 9.20 (d, J=8 Hz, 1H).

IR (CHCl$_3$) 3012, 1681, 1519, 1499, 1222 cm$^{-1}$.

MS (FD) m/e 610 (M$^+$), 610 (100).

Analytical calc'd for C$_{35}$H$_{39}$N$_5$O$_5$: C 68.94, H 6.45, N 11.49; found C 68.37, H 6.45, N 11.00.

EXAMPLE 7

[1S-(1R*, 4R*, 5S*)]-N-(1-(2-amino-2-oxoethyl)-2-oxo-3-aza-4-phenylmethyl-5-hydroxy-6-(2-(1-t-butylamino-1-oxomethyl)phenyl)hexyl)-1-oxo-2-quinolinyl carboxamide The title compound was isolated in 23% yield.

[a]$_D$+34.03° (c 0.529, MeOH).

$^1$H NMR (300 MHz, CDCl$_3$) d 1.44 (s, 9H), 2.71–2.97 (m, 5H), 3.07 (dd, J=14.3, 4.4 Hz, 1H), 3.73–3.76 (m, 1H), 4.26–4.29 (m, 1H), 4.97–4.99 (m, 1H), 5.72 (s, 1H), 5.91 (br.s, 1H), 6.28 (s, 1H), 6.33 (s, 1H), 6.84 (t, J=7.3 Hz, 1H), 7.00 (t, J=7.5 Hz, 2H), 7.09–7.33 (m, 7H), 7.67–7.87 (m, 4H), 8.21 (d, J=8.9 Hz, 1H), 8.77 (d, J=8.7 Hz, 1H), 12.05 (d, J=7.6 Hz, 1H).

IR (KBr) 3311, 3065, 2966, 1656, 1520, 1453, 1366, 735, 701 cm$^{-1}$.

Analytical calc'd for C$_{35}$H$_{39}$N$_5$O$_6$: C 67.18, H 6.26, N 11.19; found C 66.92, H 6.32, N 11.21.

EXAMPLE 8

[1S-(1R*, 4R*, 5S*)]-N-(1-(2-amino-2-oxoethyl)-2-oxo-3-aza-4-phenylmethyl-5-hydroxy-6-(2-(1-(1.1-dimethylpropylamino)-1-oxomethyl)phenyl)hexyl)-2-quinolinyl carboxamide The title compound was isolated in 34% yield.

[a]$_D$+23.60° (c 0.10, MeOH)

$^1$H NMR (300 MHz, CDCl$_3$) d 0.89 (t, J=7 Hz, 3H), 1.38 (s, 6H), 1.81 (q, J=7 Hz, 2H), 2.69 (dd, J=15, 7 Hz, 1H), 2.79–2.99 (m, 4H), 3.04 (dd, J=14, 4 Hz, 1H), 3.71–3.75 (m, 1H), 4.26–4.30 (m, 1H), 4.91–4.96 (m, 1H), 5.61 (s, 1H), 5.98 (s, 1H), 6.26 (s, 1H), 6.86–7.37 (m, 11H), 7.62 (t, J=7.5 Hz, 1H), 7.77 (t, J=7.5 Hz, 1H), 7.87 (d, J=8.2 Hz, 1H), 8.16–8.30 (m, 3H), 9.20 (d, J=8.0 Hz, 1H).

IR: (CHCl$_3$) 3410, 3028, 3010, 1681, 1518, 1499, 1428, 1234, 1048, 846 cm$^{-1}$.

MS (FD) 624(M$^+$) 624(100)

Analytical calc'd for C$_{36}$H$_{41}$N$_5$O$_5$: C 69.32, H 6.63, N 11.23; found C 69.06, H 6.76, N 10.98.

EXAMPLE 9

[1S-(1R*, 4R*, 5S*)]-N-(1-(2-amino-2-oxoethyl)-2-oxo-3-aza-4-(4-phenylmethyloxy)phenylmethyl-5-hydroxy-6-(2-(1-t-butylamino-1-oxomethyl)phenyl)hexyl)-2-quinolinyl carboxamide The title compound was isolated in 67% yield.

[a]$_D$ 0.00° (c 2.0, MeOH); [a]$_{365}$ +76.24° (c 2.0, MeOH)
$^1$H NMR (300 MHz, CDCl$_3$) d 1.44 (s, 9H), 2.72 (dd, J=15.3, 7.0 Hz, 1H), 2.81–2.99 (m, 4H), 3.08 (q, J=7.3 Hz, 1H), 3.67–3.71 (m, 1H), 4.54–4.63 (m, 2H), 4.93–4.99 (m, 1H), 5.54–5.59 (br s, 1H), 5.90 (s, 1H), 6.08–6.16 (br.s, 1H), 6.56 (d, J=8, 4 Hz, 2H), 7.06–7.13 (m, 3H), 7.25–7.37 (m, 10H), 7.59 (t , J=7.5 Hz, 1H), 7.73 (t, J=7.3 Hz, 1H), 7.84 (d, J=8.2 Hz, 1H), 8.17–8.30 (m, 3H), 9.26 (d, J=8.2 Hz, 1H).

IR (CHCl$_3$) 3410, 3025, 3011, 1680, 1512, 1500, 1454, 1367, 1218 cm$^{-1}$.

MS (FD) m/e 716 (M$^+$), 716 (100).

Analytical calc'd for C$_{42}$H$_{45}$N$_5$O$_6$: C 70.47, H 6.34, N 9.78; found C 70.65, H 6.43, N 9.74.

EXAMPLE 10

[1S-(1R*, 4R*. 5S*) ]-N-(1-(2-amino-2-oxoethyl)-2-oxo-3-aza-4-(4-hydroxyphenyl)methyl-5-hydroxy-6-(2-(1-t-butylamino-1-oxomethyl)phenyl)hexyl)-2-quinolinyl carboxamide The title compound was isolated in 87% yield.

[a]$_D$+17.43° (c 1.0, MeOH)
$^1$H NMR (300 MHz, CDCl$_3$) d 1.42 (s, 9H), 2.62–2.76 (m, 2H), 2.84–3.02 (m, 3H), 3.74–3.78 (m, 1H), 4.03–4.06 (m, 1H), 4.88–4.92 (m, 1H), 6.45 (d, J=8.3 Hz, 2H), 6.98 (d, J=8.3 Hz, 2H), 7.20–7.37 (m, 4H), 7.67 (t, J=7.5 Hz, 1H), 7.82 (t, J=7.8 Hz, 1H), 7.78–7.80 (m, 2H), 8.17 (d, J=8.1 Hz, 1H), 8.47 (s, J=8.5 Hz, 1H).

IR (KBr) 3308, 2967, 2341, 1658, 1516, 1499, 1226, 775, 733 cm$^{-1}$.

MS (FD) m/e 626 (M$^+$), 626 (100)

EXAMPLE 11

[2R-(2R*, 3S*, 6S*)]-N-t-butyl-2-(2-hydroxy-3-phenylmethyl-4-aza-5-oxo-6-(2-amino-2-oxomethyl)-6-phenylmethoxycarbonyl)hexyl)benzamide The title compound was isolated in 52% yield.

[a]$_D$ –6.72° (c 1.042, MeOH).

$^1$H NMR (300 MHz, CDCl$_3$) d 1.45 (s, 9H), 2.77–3.08 (m, 7H), 3.49 (d, J=11.1, 5.42 Hz, 1H), 3.76–3.86 (m, 1H), 4.09 (s, 1H), 4.30–4.46 (m, 1H), 5.06 (s, 2H), 5.64 (d, J=6.9 Hz, 1H), 6.04 (s, 1H), 6.80 (d, J=8.8 Hz, 1H), 7.16–7.46 (m, 14H).

IR (CHCl3) 3011, 2974, 1716, 1673, 1641, 1419, 1050 cm$^{-1}$.

MS (FD) m/e 589 (M$^+$), 589 (100) .

Analytical calc'd for C$_{33}$H$_{40}$N$_3$O$_6$: C 67.33, H 6.85, N 9.52; found C 67.21, H 6.77, N 9.41.

EXAMPLE 12

[2R-(2R*, 3S*, 6S*)]-N-t-butyl-2-(2-hydroxy-3-phenylmethyl-4-aza-5-oxo-6-hydroxymethyl-6-(N-phenylmethoxycarbonyl-amino)hexyl)benzamide The title compound was isolated in 22% yield.

[a]$_D$+2.58 (c 0.388, MeOH).

$^1$H NMR (300 MHz, CD$_3$OD) d 1.43 (s, 9H), 2.40 (dd, J=14.0, 7.7 Hz, 1H), 2.56 (dd, J=15.5, 6.1 Hz, 1H), 2.74 (dd, J=13.5, 9.9 Hz, 1H), 2.83–2.96 (m, 2H), 3.11 (dd, J=–14.0, 3.5 Hz, 1H), 3.72–3.79 (m, 1H), 4.02–4.08 (m, 1H), 4.41 (dd, J=7.6, 6.4 Hz, 1H), 5.06 (s, 2H), 7.09–7.38 (m, 14H).

IR (KBr) 3305, 3065, 2966, 1718, 1638, 1535, 1454, 1326, 1220, 1060 cm$^{-1}$.

MS (FD) m/e 562 (M$^+$), 220 (100).

EXAMPLE 13

[1S-(1R*, 4R*, 5S*)]-N-(1-(2-amino-2-oxoethyl)-2-oxo-3-aza-4-phenylmethyl-5-hydroxy-6-(2-(1-t-butylamino-1-oxomethyl)phenyl)hexyl)-1-quinolinyl-2-carboxamide The title compound was isolated in 22% yield.

[a]$_D$–9.71° (c 0.206, MeOH)

$^1$H NMR (300 MHz, CDCl$^3$) d 1.42 (s, 9H), 2.33 (br. s, 1H), 2.65 (dd, J=15.2, 6.7 Hz, 1H), 2.79–2.97 (m, 14H), 3.03 (dd, J=14.0, 3.8 Hz, 1H), 3.72 (br.m, 1H), 4.23 (br.m, 1H), 4.92 (br.m, 1H), 5.71 (br.s, 1H), 6.27 (s, 1H), 6.44 (br.s, 1H), 6.86–6.98 (m, 2H), 7.12–7.31 (m, 7H), 7.59–7.71 (m, 2H), 7.77 (d, J=5.4 Hz, 1H), 7.82 (d, J=7.94 Hz, 1H), 8.46 (d, J=5.5 Hz, 1H), 8.47 (d, J=8.0 Hz, 1H), 9.41 (d, J=8.3 Hz, 1H).

IR (CHC13) 3010, 2974, 1680, 1601, 1515, 1454, 1394, 1230 cm$^{-1}$.

MS (FD), m/e 610 (M+) , 220 (100).

EXAMPLE 14

[1S-(1R*, 4R*, 5S*)]-N-(1-(2-amino-2-oxoethyl)-2-oxo-3-aza-4-phenylmethyl-5-hydroxy-6-(2-(1-t-butylamino-1-oxomethyl)phenyl)hexyl)-2-benzimidazolyl carboxamide The title compound was isolated in 63% yield.

[a]$_D$–16.85° (c 0.53, MeOH).

$^1$H NMR (300 MHz, CD$_3$OD) d 1.43 (s, 9H), 2.59–2.77 (m, 4H), 2.93–3.00 (m, 2H), 3.14 (dd, J=12, 4 Hz, 1H), 3.72–3.83 (m, 1H), 4.06–4.13 (m, 1H), 6.81 (t, J=7 Hz, 1H), 6.97 (t, J=7.5 Hz, 2H), 7.14–7.38 (m, 8H), 7.58–7.64 (br.m, 2H).

IR (KBr) 3318, 3062, 2965, 2405, 1639, 1546, 1445, 1422, 1392, 1228 cm$^{-1}$.

MS (FD) m/e 599(M+), 599(100).

Analytical calc'd for C$_{33}$H$_{38}$N$_6$O$_5$: C 6.20, H 6.40, N 14.04; found C 66.14, H 6.56, N 13.78.

EXAMPLE 15

[2R-(2R*, 3S*, 6S*)]-N-t-butyl-2-(2-hydroxy-3-phenylmethyl-4,7-diaza-5,8,-dioxo-6-(2-amino-2-oxoethyl)-9-(naphthyloxy)nonyl)benzamide The title compound was isolated in 62% yield.

[a]$_D$–2.00° (c 1.0, MeOH)

$^1$H NMR (300 MHz, CD$_3$OD) d 1.43 (s, 9H), 2.59–2.98 (m, 6H), 3.09 (br.d, J=3.9 Hz, 1H), 3.72–3.82 (m, 1H), 4.03–4.14 (m, 1H), 4.64–4.79 (m, 2H), 6.85 (d, J=7.5 Hz, 1H), 6.97 (t, J=2.0 Hz, 1H), 7.10–7.52 (m, 12H), 7.79–7.82 (m, 1H), 8.34–8.36 (m, 1H).

IR (KBr) 3296, 3061, 2967, 2930, 2540, 2413, 1646, 1427, 1401, 1236, 768 cm$^{-1}$.

MS (FD) m/e 639(M$^+$), 639(100).

EXAMPLE 16

[1S-(1R*, 4R*, 5S*)]-N-(1-(2-propyl)-2-oxo-3-aza-4-phenylmethyl-5-hydroxy-6-(2-(1-t-butylamino-1-oxomethyl)phenyl)hexyl)-2-quinolinyl carboxamide The title compound was isolated in 13% yield.

$^1$H NMR (300 MHz, CDCl$_3$) d 0.87 (d, J=6.6 Hz, 3H), 0.97 (d, J=6.6 Hz, 3H), 1.46 (s, 9H), 2.30–2.37 (m, 1H), 2.79–3.09 (m, 4H), 3.72–3.80 (m, 1H), 4.31–4.41 (m, 2H), 5.96 (s, 1H), 6.04–6.10 (m, 1H), 6.49 (d, J=9.1 Hz, 1H), 6.80–6.89 (m, 1H), 7.04 (t, J=7.5 Hz, 1H), 7.20–7.40 (m, 7H), 7.64 (t, J=7.5 Hz, 1H), 7.80 (t, J=7.6 Hz, 1H), 7.90 (d, J=8.1 Hz, 1H), 8.16 (d, J=8.4 Hz, 1H), 8.30 (q, J=8.5 Hz, 2H), 8.53 (d, J=9.0 Hz, 1H).

MS (FAB) m/e 595 (M$^+$), 128 (100).

EXAMPLE 17

[1S-(1R*, 4R*, 5S*)]-N-(1-(4-imidazolylmethyl)-2-oxo-3-aza-4-phenylmethyl-5-hydroxy-6-(2-(1-t-butylamino-1-oxomethyl)phenyl)hexyl)-2-quinolinyl carboxamide The title compound was isolated in 84% yield.

[a]$_D$–8.46° (c 1.06, MeOH)

$^1$H NMR (300 MHz, CDCl$_3$) d 1.49 (s, 9H), 2.75–2.86 (m, 2H), 2.98–3.18 (m, 2H), 3.21 (d, J=6.5 Hz, 2H), 3.93–3.99 (m, 2H), 4.32–4.43 (m, 1H), 4.81–4.86 (m, 1H), 6.50 (br.s, 1H), 8.84 (s, 1H), 6.95–7.42 (m, 9H), 7.58–7.65 (m, 1H), 7.75–7.79 (m, 1H), 7.86 (d, J=7.5 Hz, 1H), 8.10 (d, J=8 Hz, 1H), 8.19 (d, J=7.5 Hz, 1H), 8.25 (d, J=7.5 Hz, 1H), 8.88 (d, J=8 Hz, 1H).

IR (KBr) 3700, 3276, 3010, 1656, 1601, 1518, 1500, 1455, 428, 1367, 1231, 1095, 830 cm$^{-1}$.

MS (FD) m/e 633 (M$^+$), 633 (100) .

Analytical calc'd for C$_{37}$H$_{40}$N$_6$O$_4$: C 70.23, H 6.37, N 13.28; found C 70.26, H 6.41, N 13.23.

EXAMPLE 18

[1S-(1R*, 4R*, 5S*)]-N-(1-(2-amino-2-oxoethyl)-2-oxo-3-aza-4-phenylmethyl-5-hydroxy-6-(2-(2,2-dimethyl-1-oxopropylamino)phenyl)hexyl)-2-quinolinyl carboxamide The title compound was isolated in 61% yield.

[a]$_D$–53.42° (c 1.003, MeOH)

$^1$H NMR (300 MHz, CDCl$_3$) d 1.31 (s, 9H), 2.62–3.03 (m, 6H), 4.06 (apparent dd, J=9.9 Hz, 1H), 4.17–4.22 (m, 1H), 4.85–4.91 (m, 1H), 5.52 (s, 1H), 6.00 (s, 1H), 6.94 (t, J=7.4 Hz, 1H), 7.02–7.27 (m, 9H), 7.64 (t, J=7.1 Hz, 1H), 7.77–7.81 (m, 2H), 7.86 (d, J=8.1 Hz, 1H), 8.14 (d, J=8.4 Hz, 2H), 8.27 (d, J=8.5 Hz, 1H), 9.14 (d, J=7.7 Hz, 1H), 9.23 (s, 1H).

IR (KBr) 3329, 1659, 1498, 1450, 845, 753 cm$^{-1}$.

MS (FD) m/e 610 (M$^+$), 610 (100).

Analytical calc'd for C$_{35}$H$_{39}$N$_5$O$_5$: C 68.95, H 6.45, N 11.49; found C 69.12, H 6.57, N 11.57.

EXAMPLE 19

[1S-(1R*, 4R*, 5S*)]-N-(1-(2-amino-2-oxoethyl)-2-oxo-3-aza-4-phenylmethyl-5-hydroxy-6-(2-(1-t-butylamino-1-oxomethyl)phenyl)hexyl)-2-naphthyl carboxamide Yield: 30 mg (12%) as an off-white foam $^1$H NMR (CDCl$_3$) d 8.33 (s, 1H,), 8.15 (d, 1H), 8.0–6.95 (m, 15H,), 5.98 (br.s, 2H), 5.37 (br.s, 1H), 4.89 (m, 1H), 4.3 (m, 1H), 3.78 (m, 1H), 3.1–2.58 (m, 6H), 1.45 (s, 9H). MS (FD) 609 (P+1).

EXAMPLE 20

[1S-(1R*, 4R*, 5S*)]-N-(1-(2-amino-2-oxoethyl)-2-oxo-3-aza-4-phenylmethyl-5-hydroxy-6-(2-(1-t-butylamino-1-oxomethyl)phenyl)hexyl)-2-quinoxalinyl carboxamide Yield: 29 mg (7%) of a yellowish foam $^1$H NMR (CDCl$_3$) d 9.52 (s, 1H), 9.03 (d, 1H), 8.15–6.18 (m, 13H), 6.31 (br.s, 1H), 6.15 (s, 1H), 5.92 (d, 1H), 5.7 (br.s, 1H), 4.91 (m, 1H), 4.3 (m, 1H), 3.77 (m, 1H), 3.07–2.6 (m, 6H), 1.41 (s, 9H).

MS (FD) 612 (P+2), 593, 519, 391, 307, 243, 220.

Analytical calc'd for: C$_{34}$H$_{38}$N$_6$O$_5$: C 66.87, H 6.27, N 13.76; found: C 67.14, H 6.49, N 13.56.

EXAMPLE 21

[1S-(1R*, 4R*, 5S*)]-N-(1-(2-amino-2-oxoethyl)-2-oxo-3-aza-4-phenylmethyl-5-hydroxy-6-(2-(1-t-butylamino-1-oxomethyl)phenyl)hexyl)-2-indolyl carboxamine Yield: 86 mg (16%) of a slightly colored foam.

$^1$N HMR (DMSO-d$_6$) d 11.6 (3, 1H), 8.43 (d, 1H), 8.2 (s, 1H), 7.8 (d, 1H), 7.6–7.0 (m, 13H), 5.83 (d, 1H), 4.79 (m, 1H), 3.81 (m, 1H), 3.6 (m, 1H), 3.0–2.45 (m, 6H), 1.38 (s, 9H). MS (FD) 599 (P+2).

Analytical calc'd for C$_{34}$H$_{39}$N$_5$O$_5$: C 68.32, H 6.58, N 11.71; found: C 67.69, H 6.89, N 10.42.

EXAMPLE 22

[1S-(1R*, 4R*, 5S*)]-N-(1-(2-amino-2-oxoethyl)-2-oxo-3-aza-4-phenylmethyl-5-hydroxy-6-(2-(1-t-butylamino-1-oxomethyl)phenyl)hexyl)-2-benzo[b] thienyl carboxamide Yield: 31 mg (11%) as a colorless foam.

$^1$H NMR (CDCl$_3$) d 8.17 (d, 1H), 7.85–7.0 (m, 14H), 6.03 (d, 2H), 5.41 (s, 1H), 4.82 (m, 1H), 4.3 (m, 1H), 3.78 (m, 1H), 3.1–2.6 (m, 6H), 1.5 (s, 9H). MS (FD) 616 (P12).

EXAMPLE 23

[1S-(1R*, 4R*, 5S*)]-N-(1-(2-amino-2-oxoethyl)-2-oxo-3-aza-4-phenylmethyl-5-hydroxy-6-(2-(1-t-butylamino-1-oxomethyl)phenyl)hexyl)-7-methylquinolin-2-yl carboxamide a. 2-Carboxy-7-methylquinoline By substantially following the procedures described in Shuman et al., *J. Org. Chem.*, 55, 738–741 (1990), 2-carboxy-7-methylquinoline was prepared.

b. [R-(R*, S*)]-N-t-butyl-2-(3-amino-2-hydroxypropyl) benzamide

By substantially following the procedures described in Example 1, steps a through d, the title compound was prepared.

c. [R-(R*, S*, S*)]-N-t-butyl-2-(3-N-(benzyloxycarbonyl asparginyl)amino)-2-hydroxypropyl) benzamide To 20 ml of dry dimethyl formamide (DMF) was added [R-(R*, S*)]-N-t-butyl-2-(3-amino-2-hydroxypropyl) benzamide (3.4 g; 10 mmol) from step b above; benzyloxycarbonyl-L-asparagine (2.6 g; 10 mmol); N-methylmorpholine (1.09 ml; 10 mmol); and 1-hydroxybenzotriazole hydrate (1.48 g; 11 mmol). After the solution was cooled to 0° C., 1,3-dicyclohexylcarbodiimide (2.4 g; 11 mmol) was added. The reaction mixture was allowed to warm to room temperature while stirring under a nitrogen atmosphere. After stirring overnight, the reaction mixture was filtered and the filtrate extracted with ethyl acetate. To the ethyl acetate solution was added an ethyl acetate/water mixture and the organics separated. The organics were washed sequentially with $NaHCO_3$, 5% citric acid, saturated $NaHCO_3$ and brine, then dried over $MgSO_4$. The material was evaporated to dryness, rinsed with an ether/hexane mixture and the solids filter dried in a vacuum desiccator to afford 4.4 g (78.8%) of the title compound.

d. [R-(R*, S*, S*)]-N-t-butyl-2-(3-(N-aspariginylamino)-2-hydroxypropyl)benzamide By substantially following the procedures described in Example 1, step d, the title compound was prepared.

e. [1S-(1R*, 4R*, 5S*)]-N-(1-(2-amino-2-oxoethyl)-2-oxo-3-aza-4-phenylmethyl-5-hydroxy-6-(2-(1-t-butylamino-1-oxomethyl)phenyl)hexyl)-7-methylquinolin-2-yl carboxamide To 15 ml of dry $CH_2Cl_2$ was added 2-carboxy-7-methyl quinoline (135 mg; 0.5 mmol) and 1,1-carbonyldiimidazole (81 mg; 0.5 mmol) and the mixture stirred at room temperature for 30 mintues. To the solution was added the [R-(R*, S*, S*)]-N-t-butyl-2-(3-(N-aspariginylamino)-2-hydroxypropyl)benzamide (227 mg; 0.5 mmol) from step d, above. The reaction mixture was stirred at room temperature overnight. To the reaction mixture was added $CH_2Cl_2$ (100 ml) and 25 ml of water to afford a poor emulsion. The emulsion was washed sequentially with 25 ml of saturated $NaHCO_3$; 25 ml of 5% citric acid; 25 ml of saturated $NaHCO_3$; and brine. The resulting material was dried over $MgSO_4$ and evaporated under vacuum to dryness. The residue was slurried with ether and the resulting precipitate filtered off and dried in a vacuum desiccator at room temperature to afford 115 mg (37% yield) of the title compound.

MS: FAB(M+1) 623+1

$H^1$ NMR (300 MHz, $CDCl_3$) d 1.46 (s, 9H), 2.6–3.1 (m, $3H_2$, 1H, $1CH_3$), 3.69–3.75 (m, 1H), 4.22–4.32 (m, 1H), 4.28–4.35(m, 1H), 4.9 (m, 1H), 5.3–5.35 (m, 1H), 5.9–6.05 (2 br.s, 2H), 6.89–8.3 (m, 14H), 9.3 (d, 1H).

By following the procedures described in Example 28 and employing the appropriate reactants, the compounds of Examples 29 through 35 were prepared.

EXAMPLE 24

[1S-(1R*, 4R*, 5S*)]-N-(1-(2-amino-2-oxoethyl)-2-oxo-3-aza-4-phenylmethyl-5-hydroxy-6-(2-(1-t-butylamino-1-oxomethyl)phenyl)hexyl)-8-methylquinolin-2-yl carboxamide Yield: 57.8%

MS: FAB—M+1=623+1

$^1$H NMR (300 MHz, $CDCl_3$) d 1.46 (s 9H); 2.6–3.1 (m, $3H_2$, 1H, 1CH—), 3.70–3.78, (m, 1H), 4.28–4.32 (m, 1H), 4.9 (m, 1H), 5.2 (br.s, 1H), 6.05, (br.s, 2H), 6.8–7.78, (m, 12H), 8.2–8.3 (dd, 2H).

| Analysis: | | |
|---|---|---|
| | Calculated | Found |
| C | 69.32 | 69.10 |
| H | 6.62 | 6.81 |
| N | 11.23 | 10.94 |

EXAMPLE 25

[1S-(1R*, 4R*, 5S*)]-N-(1-(2-amino-2-oxoethyl)-2-oxo-3-aza-4-phenylmethyl-5-hydroxy-6-(2-(1-t-butylamino-1-oxomethyl)phenyl)hexyl)-6-methylquinolin-2-yl carboxamide DCC (Dicyclahoxylcarbodiimide) was used as the coupling agent for the last reaction.

Yield: 54.6%

MS FAB (M+1) 623+1

$H^1$ NMR (300 MHz, $CDCl_3$) d 1.46, (s, 9H), 2.57–2.6 (s, 3H), 2.62–3.1 (m, 7H), 3.7–3.78, (m, 1H), 4.23–4.35 (m, 1H), 4.9–4.95 (m, 1H), 5.41–4.43 (br.s, 1H), 5.8–6.1 (2 br.s, 3H), 6.82–8.2 (m, 14H), 9.18–9.2 (d, 1H).

| Analysis: | | |
|---|---|---|
| | Calculated | Found |
| C | 69.32 | 69.08 |
| H | 6.62 | 6.75 |
| N | 11.23 | 10.94 |

EXAMPLE 26

[1S-(1R*, 4R*, 5S*)]-N-(1-(2-amino-2-oxoethyl)-2-oxo-3-aza-4-phenylmethyl-5-hydroxy-6-(2-(1-t-butylamino-1-oxomethyl)phenyl)hexyl)-4-methylquinolin-2-yl carboxamide Yield: 35%

MS FAB (M+1) =623+1

$^1$H NMR (300 MHz, $CDCl_3$) d 1.46, (s, 9H), 2.6–3.1 (m, 10H),3.7–3.78 (m, 1H), 4.23–4.35 (m, 1H), 4.9–4.95 (m, 1H), 5.35–5.40 (br.s, 1H), 5.97–6.08 (2 br.s, 3H), 6.82–8.2 (m, 14H), 9.18–9.2 (d, 1H).

| Analysis: | | |
|---|---|---|
| | Calculated | Found |
| C | 69.32 | 69.06 |
| H | 6.62 | 6.64 |
| N | 11.23 | 11.25 |

EXAMPLE 27

[1S-(1R*, 4R*. 5S*) ]-N-(1-(2-amino-2-oxoethyl)-2-oxo-3-aza-4-phenylmethyl-5-hydroxy-6-(2-(1-t-butylamino-1-oxomethyl)phenyl) hexyl)-3-methylquinolin-2-yl carboxamide Yield: 37%

MS FAB =correct mw of M+1=623+1.

H[1] NMR (300 MHz, CDCl$_3$) d 1.46 (s, 9H), 2.85–3.1 (m, 10H), 3.7–3.78, (m, 1H), 4.23–4.35 (m, 1H), 4.9–4.95 (m, 1H), 5.35–5.4 (br.s, 1H), 5.97–6.08, (2 br.s, 3H); 6.82–8.2 (m, 14H), 9.18–9.2 (d, 1H)

| | Analysis: | |
|---|---|---|
| | Calculated | Found |
| C | 69.32 | 68.56 |
| H | 6.63 | 6.67 |
| N | 11.23 | 10.48 |

EXAMPLE 28

[1S-(1R*, 4R*, 5S*)]-N-(1-(2-amino-2-oxoethyl)-2-oxo-3-aza-4-phenylmethyl-5-hydroxy-6-(2-(1-t-butylamino-1-oxomethyl)phenyl)hexyl)phenyl carboxamide Yield: 41.8%

H[1] NMR (300 MHz, CDCl$_3$) d 1.46 (s, 9H), 2.48–3.1 (m, 7H), 3.68–3.79 (m, 1H), 4.23–4.35 (m, 1H), 4.9–4.95 (m, 1H), 5.32–5.39, (br.s, 1H), 5.98–6.07, (br.s, 2H) 7.08–7.8 (m, 1H), (8–8.03, (d, 1H).

MS (FAB) =M+1=558+1

| | Analysis: | |
|---|---|---|
| | Calculated | Found |
| C | 68.80 | 68.56 |
| H | 6.86 | 6.92 |
| N | 10.03 | 10.00 |

EXAMPLE 29

[1S-(1R*, 4R*, 5S*)]-N-(1-(2-amino-2-oxoethyl)-2-oxo-3-aza-4-phenylmethyl-5-hydroxy-6-(2-(1-t-butylamino-1-oxomethyl)phenyl)hexyl)-2-pyridyl carboxamide The final coupling reaction was accomplished using a pentafluroactivated ester prepared substantially according to the procedures described in Preparations 2 and 3.

MS FAB =M+1=559+1

$^1$H NMR (300MHz, CDCl$_3$) d 1.46 (s, 9H), 2.59–3.1 (m, 7H), 3.68–3.79 (m, 1H), 4.23–4.35 (m, 1H), 4.85–4.92 (m, 1H), 5.39–5.43, (br.s, 1H), 5.99–6.07, (2 br.s, 3H), 6.98–7.5 (m, 10H), 7.8–7.88 (t, 1H), 8.1–8.17 (d, 1H), 8.59–8.63 (d, 1H), 9–9.05 (d, 1H).

EXAMPLE 30

[1S-(1R*, 4R*, 5S*)]-N-(1-(2-amino-2-oxoethyl)-2-oxo-3-aza-4-phenylmethyl-5-hydroxy-6-(2-(1-t-butylamino-1-oxomethyl)phenyl)hexyl)-3-isoquinolinyl carboxamide The final coupling reaction was carried out using an activated pentafluoro ester prepared according to the procedures described in Preparations 2 and 3. Yield 54.7%

MS =FAB =M+1=609+1

$^1$H NMR (300MHz, CDCl$_3$) d 1.46 (s, 9H), 2.65–3.1 (m, 7H) 3.67–3.75 (m, 1H), 4.2–4.35 (m, 1H), 4.91–4.97 (m, 1H), 5.3–5.38, (br.s, 1H), 5.8–6.03, (3 br.s, 4H), 6.9–8.1 (m, 12H), 8.3–8.39 (s, 1H), 9.19–9.13 (m, 2H).

| | Analysis: | |
|---|---|---|
| | Calculated | Found |
| C | 68.95 | 68.68 |
| H | 6.45 | 6.48 |
| N | 11.49 | 11.27 |

EXAMPLE 31

[1S-(1R*, 4R*, 5S*)]-N-(1-(2-amino-2-oxoethyl)-2-oxo-3-aza-4-phenylmethyl-5-hydroxy-6-(2-(1-t-butylamino-1-oxomethyl)phenyl)hexyl)-2-naphthyl acetamide Yield: 85 mg (62%) as a colorless foam.

$^1$H NMR (300 MHz, CDCl$_3$) d 7.82–7.05 (m, 16H), 6.93 (d, 1H), 6.05 (m, zH), 5.3 (br.s, 1H), 4.63 (m, 1H) 4.2 (m, 1H), 3.7 (s, 2H), 3.62 (m, 1H), 3.01–2.4 (m, 6H), 1.43 (s, 9H).

MS (FD) 623 (P+1).

EXAMPLE 32

[1S-(1R*, 4R*, 5S*)]-N-(1-(2-amino-2-oxoethyl)-2-oxo-3-aza-4-phenylmethyl-5-hydroxy-6-(2-(1-t-butylamino-1-oxomethyl)phenyl)hexyl)-2-quinolinoxy acetamide Yield: 90 mg (64%) of a colorless foam.

$^1$H NMR (300 MHZ, CDCl$_3$) d 8.1 (d, 1H), 7.83–6.98 (m, 16H), 6.1 (br.m, 2H), 5.41 (m, 1H), 4.79 (m, 1H), 4.56 (d, 2H), 4.25 (m, 1H), 3.71 (m, 1H), 3.02–2.5 (m, 6H), 1.43 (s, 9H). MS (FD) 640 (P+1).

EXAMPLE 33

[1S-(1R*, 4R*, 5S*)]-N-(1-(2-amino-2-oxoethyl)-2-oxo-3-aza-4-phenylmethyl-5-hydroxy-6-(2-(1-t-butylamino-1-oxomethyl)phenyl)hexyl)-2(6, 7, 8, 9-tetrahydronaphthyl) carboxamide Yield: 75 mg (54%) as a colorless foam.

$^1$H NMR (300 MHz, CDCl$_3$) d 8.0 (d, 1H), 7.5–7.03 (m, 12H), 6.51 (br.s, 1H), 6.22 (br.s, 1H), 5.57 (br.s, 1H), 4.84 (m, 1H), 4.23 (m, 1H), 3.75 (m, 1H), 3.12–2.5 (m, 10H), 1.81 (m, 4H), 1.43 (s, 9H).

MS (FD) 629 (P+1).

| | Analysis: | |
|---|---|---|
| | Calculated | Found |
| C: | 70.79 | 70.63 |
| H: | 7.55 | 7.31 |
| N: | 8.92 | 9.21 |

EXAMPLE 34

[1S-(1R*, 4R*, 5S*)]-N-(1-(1-methylethyl)-2-oxo-3-aza-4-phenylmethyl-5-hydroxy-6-(2-(1-t-butylamino-1-oxomethyl)phenyl)hexyl)-2-quinoxalinyl acetamide The title compound was prepared according to the procedures described above in Preparations 1, 2 and 3 and Example 1 using the appropriate reactants.

Yield: 51 mg (8%) as a yellowish foam.

¹H NMR (300 MHz, CDCl₃) d 9.69 (s, 1H), 8.31 (d, 1H), 8.28–7.0 (m, 13H), 6.78 (m, 2H), 6.12 (m, 2H), 4.43 (m, 2H), 3.82 (m, 1H), 1.5 (s, 9H), 1.0 (dd, 6H). MS (FD) 597 (P+1).

EXAMPLE 35

[1S-(1R*, 4R*, 5S*)]-N-(1-(1-methylethyl)-2-oxo-3-aza-4-phenylmethyl-5-hydroxy-6-(2-(1-t-butylamino-1-oxomethyl)phenyl)hexyl)-2-naphthyl acetamide The title compound was prepared according to the procedures described above in Preparation 1, 2 and 3 and Example 1 using the appropriate reactants.

Yield: 39.6 mg (11.1%) of a tan colored foam.

¹H NMR (300 MHz, CDCl₃) d 8.22 (s, 1H), 7.93–6.7 (m, 15H), 6.1 (d, 1H), 6.0 (s, 1H), 4.49 (t, 1H), 4.35 (m, 1H), 3.82 (m, 1H), 3.09–2.77 (m, 4H), 2.2 (m, 1H), 1.47 (s, 9H), 0.98 (t, 6H).

MS (FD) 594 (P+1).

EXAMPLE 36

[1S-(1R*, 4R*, 5S*)]-N-(1-(2-amino-2-oxoethyl)-2-oxo-3-aza-4-phenylmethyl-5-hydroxy-6-(2-(1-t-butylamino-1-oxomethyl)phenyl)hexyl)-3-(1,2,3,4-tetrahydroisoquinolinyl) carboxamide (Diastereomer A)

a. dl-3-carboxy-1,2,3,4-tetrahydroisoquinoline hydrochloride

By following the procedures described in Karo et al., *J. Pharm. Soc. Japan*, 94, 934 (1974) the title compound was prepared from L-phenylalanine.

b. dl-2-t-butoxycarbonyl-3-carboxy-1,2,3,4-tetrahydroisoquinoline

By following the procedures described in Bodansky and Bodansky, *The Practice of Peptide Syntheses*, Vol. 21, 20 (1984) the title compound was prepared.

c. Pentafluorophenyl ester of dl-2-Boc-3-carboxy-1,2,3,4-tetrahydroisoquinoline

The title compund was prepared according to the procedures described above in Preparation 2.

d. [R-(R*, S*, S*)]-N-t-butyl-2-(3-N-aspariginylamino)-2-hydroxypropyl)benzamide By following the procedures described in Example 28, steps b through d, the title compound was prepared.

e. dl-[1S-(1R*, 4R*, 5S*)]-N-(1-(2-amino-2-oxoethyl)-2-oxo-3-aza-4-phenylmethyl-5-hydroxy-6-(2-(1-t-butylamino- 1-oxomethyl)phenyl)hexyl-3-(2-t-butoxycarbonyl-1,2,3,4- tetrahydroisoquinolinyl carboxamide By following the procedures described in Preparation 3, except using N-methymorpholine rather than sodium bicarbonate and using dichloroethane rather than dioxane and water, the title compound was prepared.

f. dl-[1S-(1R*, 4R*, 5S*)]-N-(1-(2-amino-2-oxoethyl)-2-oxo-3-aza-4-phenylmethyl-5-hydroxy-6-(2-(1-t-butylamino-1-oxomethyl)phenyl)hexyl)-3-(1,2,3,4-tetrahydroisoquinolinyl carboxamide By following the procedures described in Bodansky and Bodansky, the practice of peptide synthesis, Vol. 21, (1984) for the removal of a Boc group, the title compound was prepared.

g. Separation of Diastereomers

The mixture of diastereomers afforded in step f, above, were separated by chromatography on silica gel using CHCL₃/CH₃OH (95:5;V:V) as eluant. Collection of fractions 2–4 afforded a single diastereomer denoted as Diastereomer A, the configuration of which around the fourth chiral atom has not been assigned.

Yield: 29 mg (38%) of a foam

¹H NMR (300 MHz, CDCl₃) d 8.25 (d, 1H), 7.4–7.0 (m, 13H), 6.35 (br.s, 1H), 6.22 (s, 1H), 5.58 (br.s, 1H), 4.68 (9, 1H), 4.29 (m, 1H), 3.95 (m, 2H), 3.75 (m, 1H), 3.52 (m, 1H), 3.1–2.43 (m, 8H), 1.47 (s, 9H).

MS (FD) 614 (P+2).

EXAMPLE 37

[1S-(1R*, 4R*, 5S*)]-N-(1-(2-amino-2-oxoethyl)-2-oxo-3-aza-4-phenylmethyl-5-hydroxy-6-(2-(1-t-butylamino-1-oxomethyl)phenyl)hexyl)-3-(1,2,3,4-tetrahydroisoquinolinyl) carboxamide (Diastereomer B)

The title compound was prepared along with Example 41 (Diastereomer A) according to steps a through f. Separation of Diastereomer B was achieved according to Example 41, Step g. Fractions 7–10 were collected and denoted Diastereomer B, the configuration of which around the fourth chiral atom has not been assigned.

Yield: 32 mg (41%) as a foam.

¹H NMR (300 MHz, CDCl₃) d 8.16 (d, 1H,) 7.46–6.9 (m, 13H), 6.62 (br.s, 1H), 6.37 (br.s, 1H), 5.9 (br.s, 1H), 4.79 (9, 1H), 4.28 (m, 1H), 3.92–3.75 (m, 3H), 3.41 (m, 1H, CH), 3.03–2.5 (m, 8H), 1.42 (s, 9H).

MS (FD) 614 (P+2).

EXAMPLE 38

[2R-(2R*, 3S*, 6S*)]-N-t-butyl-2-(2-hydroxy-3-phenylmethyl-4-aza-5-oxo-6-(1-methylpropyl)-6-(N-quinolin-2-ylmethoxycarbonylamino)hexyl) benzamide The title compound was prepared according to the general procedure outlined in Example 1. Flash chromatography with 3% MeOH/CH₂Cl₂ afforded 0.15 g of the product (68%) as a white solid.

¹H NMR (300 MHz, CDCl₃) d 0.72 (m, 6H), 1.45 (s, 9H), 1.00–1.80 (m, 3H), 2.70–3.10 (m, 6H), 3.79 (m, 1H), 3.99 (m, 1H), 4.35 (m, 1H), 5.35 (br.s, 1H), 5.43 (d, J=8 Hz, 1H), 6.24 (br.s, 1H), 6.66 (d, J=9 Hz, 1H), 7.05–7.38 (m, 9H), 7.40 (d, J=8 Hz, 1H), 7.49 (t, J=8 Hz, 1H), 7.65 (t, J=8 Hz, 1H), 7.75 (d, J=8 Hz, 1H), 7.96 (d, J=8 Hz, 1H), 8.10 (d, J=8 Hz, 1H).

IR (CHCl₃) 3429, 2970, 1725, 1645, 1601, 1515 cm⁻¹.

MS (FD) m/e 639 (M+).

Analytical calc'd for C₃₈H₄₆N₄O₅: C 71.45, H 7.26, N 8.77; found C 71.42, H 7.36, N 8.70.

EXAMPLE 39

[2R-(2R*, 3S*, 6S*)]-N-t-butyl-2-(2-hydroxy-3-phenylmethyl-4-aza-5-oxo-6-(1-methylpropyl)-7-aza-8-oxo-8-(N-methyl-N-quinolin-2-ylmethylamino)octyl)benzamide The title compound was prepared according to the general procedure outlined in Example 1. Flash chromatography with 3% MeOH/CH$_2$Cl$_2$ afforded 40 mg of the product (58%) as a white solid.

$^1$H NMR (300 MHz, CDCl$_3$) d 0.80 (m, 6H), 1.46 (s, 9H), 1.00–1.97 (m, 3H), 2.70–3.10 (m, 4H), 3.02 (s, 3H), 3.75 (m, 1H), 4.13 (t, J=6 Hz, 1H), 4.23 (m, 1H), 4.65 (s, 2H), 5.85 (d, J=5 Hz, 1H), 6.22 (s, 1H), 6.51 (d, J=9 Hz, 1H), 7.00–7.40 (m, 12H), 7.55 (t, J=8 Hz, 1H), 7.71 (t, J=8 Hz, 1H), 7.80 (d, J=8 Hz, 1H), 8.15 (d, J=8 Hz, 1H).

MS (FD) m/e 652 (M+).

Analytical calc'd for C$_{39}$H$_{49}$N$_5$O$_4$: C 71.86, H 7.58, N 10.74; found C 71.60, H 7.86, N 10.49.

EXAMPLE 40

[1S-(1R*, 4R*, 5S*)]-N-(1-(2-amino-2-oxoethyl)-2-oxo-3-aza-4-phenylmethyl-5-hydroxy-6-(2-(1-t-butylamino-1-oxomethyl)fur-3-yl)hexyl)-2-quinolinyl carboxamide The title compound was prepared according to the general procedure outlined in Example 1. Flash chromatography with 2–10% MeOH/CH$_2$Cl$_2$ afforded 80 mg of the product (44%) as a tan solid.

$^1$H NMR (300 MHz, CDCl$_3$) d 1.42 (s, 9H), 2.78 (dd, J=8 Hz, 1H), 2.85–3.10 (m, 5H), 3.74 (m, 1H), 4.25 (m, 1H), 4.97 (m, 1H), 5.38 (br.s, 1H), 5.91 (br.s, 1H), 6.49 (br.s, 1H), 6.86–7.03 (m, 5H), 7.18–7.32 (m, 4H), 7.65 (t, J=8 Hz, 1H), 7.82 (t, J=8 Hz, 1H), 7.91 (d, J=8 Hz, 1H), 8.23 (m, 2H), 8.38 (d, J=8 Hz, 1H), 9.25 (d, J=8 Hz, 1H).

IR (CHCl$_3$) 1681, 1600, 1528, 1500 cm$^{-1}$.

MS (FAB) mass 600.2839 (M+H).

Analytical calc'd for C$_{33}$HB$_7$N$_5$O$_6$: C 66.10, H 6.22, N 11.68; found C 65.93, H 6.36, N 11.40.

EXAMPLE 41

[1S-(1R*, 4R*, 5S*) ]-N-(1-(2-amino-2-oxoethyl)-2-oxo-3-aza-4-phenylmethyl-5-hydroxy-6-(2-(1-t-butylamino-1-oxomethyl)thien-3-yl)hexyl)-2-quinolinyl carboxamide The title compound was prepared according to the general procedure outlined in Example 1. HPLC with 70% MeOH/1% NH$_4$OAc in water afforded 90 mg of the product (50%) as a white solid.

$^1$H NMR (300 MHz, CDCl$_3$) d 1.42 (s, 9H), 2.75 (dd, J=7 Hz, 1H), 2.95–3.20 (m, 5H), 3.77 (m, 1H), 4.27 (m, 1H), 4.95 (m, 1H), 5.38 (br.s, 1H), 5.93 (br.s, 1H), 6.41 (br.s, 1H), 6.95 (m, 5H), 7.20 (m, 4H), 7.66 (t, J=8 Hz, 1H), 7.81 (t, J=8 Hz, 1H), 7.90 (d, J=8 Hz, 1H), 8.20 (m, 2H), 8.34 (d, J=8 Hz, 1H), 9.25 (d, J=8 Hz, 1H).

IR (KBr) 3302, 1667, 1498, 1427 cm$^{-1}$.

MS (FAB) mass 616.2591 (M+H), (FD) m/e 615 (M+).

Analytical calc'd for C$_{33}$H$_{37}$N$_5$O$_5$S: C 64.37, H 6.06, N 11.37; found C 64.60, H 5.98, N 11.42.

EXAMPLE 42

[1S-(1R*, 4R*, 5S*)]-N-(1-(2-amino-2-oxoethyl)-2-oxo-3-aza-4-phenylmethyl-5-hydroxy-6-(2-(1-t-butylamino-1-oxomethyl)benzofur-3-yl)hexyl)-2-quinolinyl carboxamide The title compound was prepared according to the general procedure outlined in Example 1. Flash chromatography with 5% MeOH/CH$_2$Cl$_2$ afforded 0.25 g of the product (86%) as a white solid.

$^1$H NMR (300 MHz, CDCl$_3$) d 1.42 (s, 9H), 2.75–3.40 (m, 6H), 3.80 (m, 1H), 4.37 (m, 1H), 5.00 (m, 1H), 5.61 (br.s, 1H), 6.30 (br.s, 1H), 6.61 (br.s, 1H), 6.80–7.40 (m, 11H), 7.62 (t, J=8 Hz, 1H), 7.75 (t, J=8 Hz, 1H), 7.85 (d, J=8 Hz, 1H), 8.20 (m, 2H), 8.27 (d, J=8 Hz, 1H), 9.27 (d, J=8 Hz, 1H).

IR (KBr) 3411, 1680, 1603, 1523, 1500 cm$^{-1}$.

MS (FD) m/e 650 (M+).

Analytical calc'd for C$_{37}$H$_{39}$N$_5$O$_6$: C 68.40, H 6.05, N 10.78; found C 68.19, H 6.01, N 11.07.

EXAMPLE 43

[1S-(1R*, 4R*, 5S*)]-N-(1-(2-hydroxy-2-oxoethyl)-2-oxo-3-aza-4-phenylmethyl-5-hydroxy-6-(2-(1-t-butylamino-1-oxomethyl)phenyl)hexyl)-2-quinolinyl carboxamide The final coupling reaction was accomplished using an activated pentafluoro ester prepared according to the procedures described in Preparations 2 and 3.

Yield: 40 mg (40%) of a colorless solid.

$^1$H NMR (300 MHz, DMSO-d$_6$) d 1.38 (s, 9H), 2.58–3.05 (m, 6H), 3.61 (br.s, 1H), 3.84 (m, 1H), 4.79 (m, 1H), 5.88 (s, 1H), 6.92 (t, J=8 Hz, 1H), 7.02 (t, J=8 Hz, 2H), 7.12–7.37 (m, 6H), 7.75 (t, J=10 Hz, 2H), 7.90 (t, J=10 Hz, 2H), 7.98 (d, J=10 Hz, 2H), 8.07–8.23 (m, 4H), 8.60 (d, J=10 Hz, 1H), 8.89 (d, J=10 Hz, 1H), 12.40 (s, 1H).

MS (FD) m/e 613 (25), 612 (95), 611 (100).

Analytical calc'd for C$_{35}$H$_{38}$N$_4$O$_6$: C 68.84, H 6.27, N 9.17; found C 68.61, H 6.44, N 9.10.

EXAMPLE 44

[1S-(1R*, 4R*, 5S*)]-N-(1-(3-hydroxy-3-oxopropyl)-2-oxo-3-aza-4-phenylmethyl-5-hydroxy-6-(2-(1-t-butylamino-1-oxomethyl)phenyl)hexyl)-2-quinolinyl carboxamide The final coupling reaction was accomplished using an activated pentafluoro ester prepared according to the procedures described in Preparations 2 and 3.

Yield: 0.58 g (98%) of a colorless solid.

$^1$H NMR (300 MHz, DMSO-d$_6$) d 1.34 (s, 9H), 1.96 (m, 2H), 2.17 (t, J=6 Hz, 2H), 2.60–2.76 (m, 2H), 2.88 (d, J=15 Hz, 1H), 3.02 (d, J=15 Hz, 1H), 3.91 (br.s, 1H), 4.07 (br.s, 1H), 4.48 (m, 1H), 5.83 (br.s, 1H), 6.98 (t, J=9 Hz, 1H), 7.10 (t, J=9 Hz, 2H), 7.15–7.35 (m, 6H), 7.72 (t, J=9 Hz, 1H), 7.87 (t, J=9 Hz, 1H), 8.03–8.20 (m, 5H), 8.50 (d, J=9 Hz, 1H), 8.72 (d, J=9 Hz, 1H). MS (FD) m/e 626 (15), 625 (35), 220 (8).

Analytical calc'd for C$_{36}$H$_{40}$N$_4$O$_6$: C 69.21, H 6.45, N 8.97; found C 68.93, H 6.32, N 8.95.

EXAMPLE 45

[1S-[1R*, 4R*, 5S*)]-N-(1-(2-(N-2-pyridylmethyl)amino)-2-oxoethyl]-2-oxo-3-aza-4-phenylmethyl-5-hydroxy-6-(2-(1-t-butylamino-1-oxomethyl)phenyl)hexyl)-2quinolinyl carboxamide The title compound was prepared according to the general procedure outlined in Example 1, using 0.2 g (0.33 mmol) of [1S-(1R*, 4R*, 5S*)]-N-(1-(2-hydroxy-2-oxoethyl)-2-oxo-3-aza-4-phenylmethyl-5-hydroxy-6-(2-(1-t-butylamino-1-oxomethyl)phenyl)hexyl)-2-quinolinyl carboxamide, from Example 48, and 0.07 mL (0.66 mmol)

of 2-aminomethylpyridine. The coupling agent for the reaction was carbonyldiimidazole. Flash chromatography using a silica column with 2.5% MeOH/EtOAc containing a trace of NH4OH afforded 33 mg (14%), of the desired product as a single diastereomer, as determined by 300 MHz $^1$H NMR.

$^1$H NMR (300 MHz, CDCl$_3$) d 1.48 (s, 9H), 2.77–3.16 (m, 6H), 3.80 (br.s, 1H), 4.33 (m, 1H), 4.59 (m, 2H), 5.02 (m, 1H), 5.90 (br.s, 1H), 6.23 (s, 1H), 6.90–7.09 (m, 4H), 7.15 (m, 1H), 7.20–7.42 (m, 8H), 7.57–7.70 (m, 2H), 7.82 (t, J=8 Hz, 1H), 7.91 (d, J=8 Hz, 1H), 8.18–8.40 (m, 4H), 9.35 (d, J=8 Hz, 1H).

MS (FD) m/e 701 (100), 700 (15), 481 (28), 220 (90).

Analytical calc'd for C$_{41}$H$_{44}$N$_6$O$_5$·2.2H$_2$O: C 66.50, H 6.56, N 11.40; found C 66.35, H 6.20, N 11.00.

EXAMPLE 46

[1S-(1R*, 4R*, 5S*)]-N-(1-(2-(N-2-imidazolylmethyl)amino)-2-oxoethyl)-2-oxo-3-aza-4-phenylmethyl-5-hydroxy-6-(2-(1-t-butylamino-1-oxomethyl)phenyl)hexyl)-2-quinolinyl carboxamide The title compound was prepared according to the general procedure outlined in Example 1, using 0.50 g (0.82 mmol) of [1S-(1R*, 4R*, 5S*)]-N-(1-(2-hydroxy-2-oxoethyl)-2-oxo-3-aza-4-phenylmethyl-5-hydroxy-6-(2-(1-t-butylamino-1-oxomethyl)phenyl)hexyl)-2-quinolinyl carboxamide, from Example 48, and 0.28 g (1.64 mmol) of imidazolemethylamine dihydrochloride. Flash chromatography with 5% MeOH/EtOAc containing a trace of NH$_4$OH afforded 0.26 g (46%) of a colorless solid.

$^1$H NMR (300 MHz, DMSO-d$_6$) d 1.33 (s, 9H), 2.69 (m, 5H), 2.95 (dd, J=30 Hz, 14, 2H), 3.62 (br.s, 1H), 3.88 (br.s, 1H), 4.22 (d, J=10 Hz, 2H), 4.80 (br. s, 1H), 6.82 (br. s, 1H), 6.87 (t, J=8 Hz, 1H), 7.05 (t, J=8 Hz, 2H), 7.15–7.25 (m, 4H), 7.30 (t, J=7 Hz, 2H), 7.74 (t, J=7 Hz, 1H), 7.89 (t, J=9 Hz, 1H), 7.98–8.14 (m, 6H), 8.45 (t, J=6 Hz, 1H), 8.58 (d, J=9 Hz, 1H), 8.96 (d, J=9 Hz, 1H).

MS (FD) m/e 691 (80), 690 (100).

Analytical calc'd for C$_{39}$H$_{43}$N$_7$O$_5$: C 67.91, H 6.28, N 14.21; found C 67.67, H 6.50, N 13.98.

EXAMPLE 47

[1S-(1R*, 4R*, 5S*)]-N-(1-(2-(N-benzyloxy)amino)-2-oxoethyl)-2-oxo-3-aza-4-phenylmethyl-5-hydroxy-6-(3-(1-t-butylamino-1-oxomethyl)phenyl)hexyl)-2-quinolinyl carboxamide The title compound was prepared according to the general procedure outlined in Example 51. Flash chromatography with 10% MeOH/CH$_2$Cl$_2$ afforded 0.189 g (92%) of a white solid.

$^1$H NMR (300 MHz, DMSO-d$_6$) d 1.35 (s, 9H), 2.52 (s, 1H), 2.61–2.73 (m, 2H), 2.87–3.03 (m, 2H), 3.60–3.64 (m, 1H), 3.85–3.89 (m, 1H), 4.64 (d, j =5.9 Hz, 1H), 4.78 –4.83 (m, 1H), 5.84 (d, J=5.6 Hz, 1H), 6.90–6.95 (m, 1H), 7.03 (t, J=7.5 Hz, 2H), 7.13–7.37 (m, 13H), 7.73 (t, J=7.5 Hz, 1H), 7.86–7.91 (m, 1H), 8.01–8.20 (m, 5H), 8.60 (d, J=8.6 Hz, 1H), 8.83 (d, J=8.5 Hz, 1H), 11.10 (s, 1H).

IR (KBr) 3319, 2929, 1652, 1522, 1498, 1454, 1366, 1221, 846, 748, 699 cm$^{-1}$.

MS (FD) m/e 717 (M+1, 24), 632 (21), 610 (100), 593 (9), 518 (6), 389 (17), 220 (68).

Analytical calc'd for C$_{42}$H$_{45}$N$_5$O$_6$: C 70.47, H 6.34, N 9.78; found C 70.77, H 6.63, N 9.66.

EXAMPLE 48

[1S-(1R*, 4R*, 5S*)]-N-(1-(2-(N-pyrid-4-yl)amino)-2-oxoethyl)-2-oxo-3-aza-4-phenylmethyl-5-hydroxy-6-(2-(1-t-butylamino-1-oxomethyl)phenyl)hexyl)-2-quinolinyl carboxamide The title compound was prepared according to the general procedure outlined in Example 51. Flash chromatography with 3–10% MeOH/CH$_2$Cl$_2$ afforded 0.007 g (3%) of a white solid.

$^1$H NMR (300 MHz, (DCl$_3$) d 1.46 (s, 9H), 2.76–3.14 (m, 7H), 3.74–3.83 (m, 1H), 4.33–4.41 (m, 1H), 5.03–5.09 (m, 1H), 5.97 (s, 1H), 6.10–6.14 (m, 1H), 6.88 (d, J=7 Hz, 1H), 6.94–7.03 (m, 3H), 7.18 (d, J=9 Hz, 2H), 7.26 (s, 1H), 7.33–7.43 (m, 4H), 7.66 (t, J=9 Hz, 1H), 7.80 (t, J=9 Hz, 1H), 7.92 (d, J=9 Hz), (H), 8.17 (d, J=9 Hz, 1H), 8.28 (s, 1H), 8.32 (s, 1H) 8.37 (d, J=8 Hz, 2H), 8.93 (s, 1H), 9.13 (d, J=8 Hz, 1H).

MS (FD) m/e 688 (M+I, 100), 220 (22).

EXAMPLE 49

[1S-(1R*, 4R*, 5S*)]-N-(1-(2-(N-2-benzimidazolylmethyl)amino)-2-oxoethyl)-2-oxo-3-aza-4-phenylmethyl-5-hydroxy-6-(2-(1-t-butylamino-1-oxomethyl)phenyl)hexyl)-2-quinolinyl carboxamide The title compound was prepared according to the general procedure outlined in Example 51. Flash chromatography with 3–10% MeOH/CH$_2$Cl$_2$ afforded 0.199 g (82%) of a yellow foam.

$^1$H NMR (300 MHz, DMSO-d$_6$) d 1.34 (s, 9H), 2.63–3.30 (m, 5H), 3.60–3.65 (m, 1H), 3.88–3.91 (m, 1H), 4.43 (d, J=5.6 Hz, 2H), 4.84 (dd, J=7.8 Hz; 6.0, 1H), 5.87 (d, J=5.3 Hz, 1H), 6.92–7.47 (m, 14H), 7.69–7.75 (m, 1H), 7.85 (t, J=7.7 Hz, 1H), 8.03–8.20 (m, 6H), 8.57 (d, J=8.6 Hz, 1H), 8.65 (m, 1H), 9.00 (d, J=8.2 Hz, 1H).

MS (FD) m/e 743 (M+i), 740 (29), 739 (50), 354 (100).

Analytical calc'd for C$_{43}$H$_{45}$N$_7$O$_5$·0.4H$_2$O: C 69.13, H 6.18, N 13.12; found C 68.84, H 6.35, N 13.50.

EXAMPLE 50

[1S-(1R*, 4R*, 5S*)]-N-(1-(2-(N-(N-3-pyridyl)amino)amino)-2-oxoethyl)-2-oxo-3-aza-4-phenylmethyl-5-hydroxy-6-(2-(1-t-butylamino-1-oxomethyl)phenyl)hexyl)-2-quinolinyl carboxamide The title compound was prepared according to the general procedure outlined in Example 51. Flash chromatography with 3–10% MeOH/CH$_2$Cl$_2$ afforded 0.171 g (74.5%) of an orange solid.

$^1$H NMR (300 MHz, DMSO-d$_6$) d 1.35 (s, 9H), 2.63–2.82 (m, 4H), 2.88–3.02 (m, 2H), 3.59–3.63 (m, 1H), 3.87–3.90 (m, 1H), 4.80–4.88 (m, 1H), 5.82 (d, J=5.4 Hz, 1H), 6.46–6.51 (m, 2H), 6.93–6.97 (m, 1H), 7.05 (t, J=7.4 Hz, 1H), 7.16–7.22 (m, 4H), 7.28–7.32 (m, 2H), 7.71–7.75 (m, 1H), 7.86–7.91 (m, 2H), 8.03 (d, J=8.9 Hz, 1H), 8.08–8.19 (m, 5H), 8.61 (d, J=8.5 Hz, 1H), 8.92 (d, J=8.4 Hz, 1H), 9.79 (s, 1H).

MS (FD) m/e 702 (M—, 100).

Analytical calc'd for C$_{40}$H$_{43}$N$_7$OS: C 68.46, H 6.18, N 13.97; found C 65.74, H 6.26, N 14.22.

EXAMPLE 51

[1S-(1R*, 4R*. 5S*)]-N-(1-(2-amino-2-oxoethyl)-2-oxo-3-aza-4-cyclohexylmethyl-5-hydroxy-6-(2-(1-t-butylamino-1-oxomethyl)phenyl)hexyl)-2-quinolinyl carboxamide The title compound was prepared according to the general procedure outlined in Example 1. Flash chromatography with 5% MeOH in CH$_2$Cl$_2$ containing a trace of NH$_4$OH afforded 0.63 g (71%) of an off-white solid.

$^1$H NMR (300 MHz, CDCl$_3$) d 1.44 (s, 9H), 0.71–1.66 (m, 8H), 1.82 (d, J=11 Hz, 1H), 5.60 (s, 1H), 6.33 (br.s), 2H), 7.11 (d, J=10 Hz, 1H), 7.18–7.41 (m, 6H), 7.66 (t, J=9 Hz, 1H), 7.81 (t, J=9 Hz, 1H), 7.90 (d, J=9 Hz, 1H), 8.27 (t, J=9 Hz, 2H), 8.37 (d, J=9 Hz, 1H), 9.48 (d, J=9 Hz, 1H).

MS (FD) m/e 616 (100), 396 (15), 395 (33), 394 (8), 221 (18), 220 (100), 192 (20), 191 (88).

Analytical calc'd for $C_{35}H_{45}N_5O_5$: C 68.27, H 7.37, N 11.37; found: C 68.47, H 7.48, N 11.62.

EXAMPLE 52

[1S-(1R*, 4R*, 5S*)]-N-(1-(2-amino-2-oxoethyl)-2-oxo-3-aza-4-phenylmethyl-5-hydroxy-6-(2-(1-t-butylamino-1-oxomethyl)phenyl)hexyl)-8-fluoroquinolin-2-yl carboxamide The title compound was prepared according to the general procedure outlined in Example 1, using carbonyldiimidazole as a coupling agent. Yield: 158 mg (25%).

$^1$H NMR (300 MHz, CDCl$_3$) d 1.4 (s, 9H), 2.7–3.1 (m, 6H), 3.7–3.8 (m, 1H), 4.3–4.4 (m, 1H), 4.9–5.0 (m, 1H), 5.44 (m, 1H), 6.0–6.1 (m, 2H), 6.9–7.7 (m, 14H), 8.3–8.4 (2d, 2H), 9.2 (d, 1H).

MS (FD) 627.

Analytical calc'd for $C_{35}H_{38}N_5O_5F$: C 66.97, H 6.10, N 11.16; found C 67.21, H 6.22, N 11.03.

EXAMPLE 53

[1S-(1R*, 4R*, 5S*)]-N-(1-(2-amino-2-oxoethyl)-2-oxo-3-aza-4-phenylmethyl-5-hydroxy-6-(2-(1-t-butylamino-1-oxomethyl)phenyl)hexyl)-4-chloroquinolin-2-yl carboxamide The title compound was prepared according to the general procedure outlined in Example 57. Yield: 29.2 mg (9%).

$^1$H NMR (300 MHz, CDCl$_3$) d 1.45 (s, 9H), 2.7–3.1 (m, 6H), 3.7–3.8 (m, 1H), 4.3–4.4 (m, 1H), 4.9–5.0 (m, 1H), 5.5 (m, 1H), 6.0 (m, 2H), 6.9–8.3 (m, 17H), 9.2 (d, 1H).

MS (FD) 644.

Analytical calc'd for $C_{35}H_{38}N_5O_5Cl$: C 65.26, H 5.95, N 10.87; found C 65.55, H 6.04, N 10.85.

EXAMPLE 54

[1S-(1R*, 4R*, 5S*)]-N-(1-(3-amino-3-oxopropyl)-2-oxo-3-aza-4-phenylmethyl-5-hydroxy-6-(2-(1-t-butylamino-1-oxomethyl)phenyl)hexyl)-2-quinolinyl carboxamide The title compound was prepared according to the general procedure outlined in Example 1. Yield: 15 mg (12.6%).

$^1$H NMR (300 MHz, CDCl$_3$) d 1.45 (s, 9H), 2–2.3 (m, 4H), 2.8–3.1 (m, 4H), 3.91 (m, 1H), 4.39 (m, 1H), 4.64 (m, 1H), 5.6 (br.s, 1H), 6.03 (br.d, 1H), 6.2 (br.s, 1H), 6.5 (br.s, 1H), 6.97 (m, 1H), 7.08–7.4 (m, 9H), 7.65 (t, 1H), 7.8 (t, 1H), 7.89 (d, 1H), 8.14–8.32 (m, 3H), 8.8 (d, 1H).

MS (FD) 624 (P+2), 603, 532, 403, 220.

Analytical calc'd for $C_{36}H_{41}N_5O_5$: C 71.36, H 6.80, N 9.00; found C 70.61, H 6.92, N 8.82.

EXAMPLE 55

[1S-(1R*, 4R*, 5S*)]-N-(1-(2-amino-2-oxoethyl)-2-oxo-3-aza-4-phenylmethyl-5-hydroxy-6-(2-(1-t-butylamino-1-oxomethyl)phenyl)hexyl)-6-chloroquinolin-2-yl carboxamide The title compound was prepared according to the general procedure outlined in Example 57. Yield: 40 mg (6%).

$^1$H NMR (300 MHz, CDCl$_3$) d 1.4 (s, 9H), 2.6–3.1 (m, 6H), 3.7–3.8 (m, 1H), 4.3–4.4 (m, 1H), 4.9–5.0 (m, 1H), 5.4 (m, 1H), 5.9–6.0 (m, 2H), 6.9–8.25 (m, 16H), 9.2 (d, 1H).

MS (FAB) 644.

Analytical calc'd for $C_{35}H_{38}N_5O_5Cl$: C 65.26, H 5.95, N 10.87; found C 66.38, H 6.11, N 10.86.

EXAMPLE 56

[1S-(1R*, 4R*, 5S*)]-N-(1-(3-amino-3-oxopropyl)-2-oxo-3-aza-4-phenylmethyl-5-hydroxy-6-(2-(1-t-butylamino-1-oxomethyl)phenyl)hexyl)-2-naphthyl carboxamide The title compound was prepared according to the general procedure outlined in Example 1. Yield: 45 mg (35%).

$^1$H NMR (300 MHz, CDCl$_3$) d 1.49 (s, 9H), 2.1–2.3 (m, 4H), 2.8–3.13 (m, 4H), 3.87 (m, 1H), 4.35 (m, 1H), 4.66 (9, 1H), 5.82 (br.s, 1H), 6.04 (d, 1H), 6.29 (s, 1H), 6.57 (br.s, 1H), 6.98–7.93 (m, 17H), 8.29 (s, 1H).

MS (FD) 623 (P+), 605, 531, 220.

Analytical calc'd for $C_{37}H_{42}N_4O_5$: C 71.36, H 6.80, N 9.00; found C 70.61, H 6.92, N 8.82.

EXAMPLE 57

[2R-(2R*, 3S*, 6S*)]-N-t-butyl-2-(2-hydroxy-3-phenylmethyl-4-aza-5-oxo-6-(2-amino-2-oxoethyl)-7-aza-8-oxo-8-(N-benzylamino)octyl)benzamide A solution of 60 mg (0.131 mmol) of [2R-(2R*, 3S*, 6S*)]-N-t-butyl-2-(2-hydroxy-3-phenylmethyl-4-aza-5-oxo-6-(2-amino-2-oxoethyl)-6-aminohexyl)benzamide and 0.02 mL (0.158 mmol) of benzylisocyanate in 2 mL of THF was prepared, under nitrogen. This solution was stirred at room temperature for 2 hours, resulting in the formation of a colorless precipitate The solid was collected by filtration, washed with cold THF and dried in vacuo to afford 15 mg of a colorless solid.

$^1$H NMR (300 MHz, DMSO-d$_6$) d 1.32 (s, 9H), 2.29–3.0 (m, 6H), 3.57 (m, 1H), 3.8 (m, 2H), 4.18 (d, 1H), 4.32 (m, 1H), 5.79 (d, 1H), 6.14 (d, 1H), 6.62 (t, 1H), 6.82 (br.s, 1H), 7.03–7.3 (m, 14H), 7.71 (d, 1H), 8.19 (s, 1H).

MS (FD) 588 (P), 481, 367, 220.

Analytical calc'd for $C_{33}H_{41}N_5O_5$: C 67.44, H 7.03, N 11.92; found C 67.20, H 7.13, N 12.18.

EXAMPLE 58

[2R-(2R*, 3S*, 6S*)]-N-t-butyl-2-(2-hydroxy-3-phenylmethyl-4-aza-5-oxo-6-(2-amino-2-oxoethyl)-7-aza-8-oxo-8-(N-naphth-1-ylmethylamino)octyl)benzamide The title compound was prepared according to the general procedure outlined in Example 62 to afford 116.5 mg (69%) of a colorless solid.

$^1$H NMR (300 MHz, DMSO-d$_6$) d 1.39 (s, 9H), 2.3–3.0 (m, 6H), 3.55 (m, 1H), 3.84 (m, 1H), 4.35 (9,1H), 4.65 (d, 2H), 5.82 (d, 1H), 6.19 (d, 1H), 6.7 (t, 1H), 6.86 (br.s, 1H), 7.41–7.4 (m, 11H), 7.54 (m, 2H), 7.73 (d, 1H), 7.8 (m, 1H), 7.91 (m, 1), 8.04 (m, 1H), 8.2 (s, 1H).

MS (FD) 638 (P+1).

Analytical calc'd for $C_{37}H_{43}N_5O_5$: C 69.68, H 6.80, N 10.98; found C 69.54, H 6.70, N 10.74.

EXAMPLE 59

[1S-(1R*, 4R*, 5S*)]-N-(1-(2-amino-2-oxoethyl)-2-oxo-3-aza-4-phenylmethyl-5-hydroxy-6-(2-(1-t-butylamino-1-oxomethyl)phenyl)hexyl)-6,8-difluoroquinolin-2-yl carboxamide The title compound was prepared according to the general procedure outlined in Example 57. Yield: 51.3 mg (8%).

¹H NMR (300 MHz, CDCl₃) d 1.4 (s, 9H), 2.6–3.1 (m, 6H), 3.7–3.8 (m, 1H), 4.3–4.4 (m, 1H), 4.9–5.0 (m, 1H), 5.3–5.4 (m, 1H), 5.9 (m, 1H), 6.0 (m, 1H), 6.6–7.4 (m, 13H), 8.3 (s, 2H), 9.2 (d, 1H).

MS (FD) 646 (M+1).

Analytical calc'd for $C_{35}H_{37}N_5OSF_2$: C 65.10, H 5.78, N 10.84; found C 65.64, H 6.47, N 11.68.

EXAMPLE 60

[1S-1R*, 4R*, 5S*)]-N-(1-(2-amino-2-oxoethyl)-2-oxo-3-aza-4-phenylmethyl-5-hydroxy-6-(2-(1-t-butylamino-1-oxomethyl)phenyl)hexyl)-4-chloro-8-isopropylquinolin-2-yl carboxamide The title compound was prepared according to the general procedure outlined in Example 57. Yield: 38.5 mg (3%).

¹H NMR (300 MHz, CDCl₃) d 1.4–1.5 (m, 15H), 2.6–3.1 (m, 6H), 3.7–3.8 (m, 1H), 4.3–4.4 (m, 2H), 4.9–5.0 (m, 1H), 5.3 (m, 1H), 5.9–6.0 (m, 2H), 6.9–7.4 (m, 10H), 7.7–7.8 (m, 2H), 8.1–8.2 (d, 2H), 8.3 (s, 1H), 9.2 (d, 1H).

MS (FD) 686.

EXAMPLE 61

[1S-(1R*, 4R*, 5S*)]-N-(1-(2-amino-2-oxoethyl)-2-oxo-3-aza-4-phenylmethyl-5-hydroxy-6-(2-(1-t-butylamino-1-oxomethyl)phenyl)hexyl)-8-quinolinyl carboxamide The title compound was prepared according to the general procedure outlined in Example 57.

¹H NMR (300 MHz, DMSO-d₆) d 1.3 (s, 9H), 2.2–3.0 (m, 6H), 3.6 (m, 1H), 3.8 (m, 1H), 4.3–4.4 (m, 1H), 5.8 (d, 1H), 6.4 (d, 1H), 6.8 (s, 1H), 7.1–7.4 (m, 16H), 7.6 (d, 1H), 8.2 (d, 1H).

MS (FD) 644.

EXAMPLE 62

[1S-(1R*, 4R*, 5S*)]-N-(1-(2-amino-2-oxoethyl)-2-oxo-3-aza-4-phenylmethyl-5-hydroxy-6-(2-(1-t-butylamino-1-oxomethyl)phenyl)hexyl)-8-chloroquinolin-2-yl carboxamide The title compound was prepared according to the general procedure outlined in Example 57. yield: 62.5 mg (18%).

¹H NMR (300 MHz, CDCl₃) d 1.4 (s, 9H), 2.2–3.1 (m, 6H), 3.7 (m, 1H), 4.3–4.4 (m, 1H), 4.8–4.9 (m, 1H), 5.4 (m, 1H), 5.9 (m, 1H), 6.0 (m, 1H), 6.9–8.4 (m, 14H), 9.4 (d, 1H).

MS (FD) 644.

Analytical calc'd for $C_{35}H_{38}N_5O_5Cl$: C 65.26, H 5.95, N 10.87; found C 65.50, H 6.04, N 10.94.

EXAMPLE 63

[1S-(1R*, 4R*, 5S*)]-N-(1-(2-amino-2-oxoethyl)-2-oxo-3-aza-4-phenylmethyl-5-hydroxy-6-(2-(1-t-butylamino-1-oxomethyl)phenyl)hexyl)-5,7-dimethylquinolin-2-yl carboxamide The title compound was prepared according to the general procedure outlined in Example 1. Chromatography over a silica column with 0–5% MeOH in CHCl₃ afforded 0.52 g (74%).

¹H NMR (300 MHz, CDCl₃) d 1.48 (s, 9H), 2.57 (s, 3H), 2.72 (s, 3H), 2.71–3.18 (m, 5H), 3.68–3.8 (m, 2H), 4.25–4.39 (m, 1H), 4.91–5.0 (m, 1H), 5.36 (s, 1H), 6.07 (s, 2H), 6.9–7.13 (m, 5H), 7.20–7.42 (m, 8H), 7.92 (s, 1H), 8.21 (d, J=8 Hz, 1H), 8.48 (d, J=8 Hz, 1H), 9.38 (d, J=5 Hz, 1H).

MS (FD) 638, 546.

Analytical calc'd for $C_{37}H_{43}N_5O_5$: C 69.68, H 6.80, N 10.98; found C 69.83, H 6.99, N 10.93.

EXAMPLE 64

[1S-(1R*, 4R*, 5S*)]-N-(1-(2-amino-2-oxoethyl)-2-oxo-3-aza-4-phenylmethyl-5-hydroxy-6-(2-(1-t-butylamino-1-oxomethyl)phenyl)hexyl)-4-methoxyquinolin-2-yl carboxamide The title compound was prepared according to the general procedure outlined in Example 1. Chromatography over a silica column with 0–5% MeOH in CHCl₃ afforded 560 mg (80%).

¹H NMR (300 MHz, CDCl₃) d 1.47 (s, 9H), 2.68–3.13 (m, 6H), 3.72–3.82 (m, 1H), 4.16 (s, 3H), 4.23–4.39 (m, 1H), 4.92–5.02 (m, 1H), 5.48 (br.s, 1H), 5.85–6.24 (m, 3H), 6.92–7.41 (m, 9H), 7.58–7.84 (m, 3H), 9.32–9.48 (br.s, 1H).

MS (FD) 640, 420, 220.

EXAMPLE 65

[1S-(1R*, 4R*, 5S*)]-N-(1-(2-amino-2-oxoethyl)-2-oxo-3-aza-4-phenylmethyl-5-hydroxy-6-(2-(1-t-butylamino-1-oxomethyl)-5-methylphenyl)hexyl)-2-quinolinyl carboxamide The title compound was prepared according to the general procedure outlined in Example 1. Chromatography over a silica column with 1–5% MeOH in CH₂Cl₂ afforded a white solid.

¹H NMR (300 MHz, CDCl₃) d 1.45 (s, 9H), 2.35 (s, 3H), 2.68–3.12 (m, 6H), 3.70–3.78 (m, 1H), 4.25–4.38 (m, 1H), 4.95–5.02 (m, 1H), 6.00 (s, 1H), 6.05 (br.s, 1H), 6.89–7.30 (m, 8H), 7.64–7.96 (m, 3H), 8.2–8.4 (m, 3H), 9.28 (d, J=6 Hz, 1H).

MS (FAB) 624, 607, 355.

Analytical calc'd for $C_{36}H_{41}N_5O_5$: C 69.32, H 6.62, N 11.23; found C 69.50, H 6.71, N 11.31.

EXAMPLE 66

[1S-(1R*, 4R*, 5S*)]-N-(1-(3-amino-2-oxoethyl)-2-oxo-3-aza-4-phenylmethyl-5-hydroxy-6-(2-(1-t-butylamino-1-oxomethyl)phenyl)hexyl)-4-(2,2-dimethylethyl)quinolin-2-yl carboxamide The title compound was prepared according to the general procedure outlined in Example 1. Chromatography over a silica column with 0–5% MeOH in CHCl₃ afforded 641 mg (87%).

¹H NMR (300 MHz, CDCl₃) d 0.88 (t, J=7 Hz, 3H), 1.45 (s, 9H), 1.73 (d, J=7 Hz, 3H), 1.69–1.79 (m, 2H), 2.68–3.12 (m, 7H), 3.70–3.79 (m, 1H), 4.26–4.37 (m, 1H), 4.92–5.01 (m, 1H), 5.55 (br.s, 1H), 6.12–6.22 (m, 2H), 6.91–7.40 (m, 10H), 7.63–7.72 (m, 2H), 8.13–8.31 (m, 3H), 9.23 (d, J=8 Hz, 1H).

MS (FD) 666, 573,445.

Analytical calc'd for $C_{29}H_{47}N_5O_5$: C 70.35, H 7.12, N 10.52; found C 70.09, H 7.03, N 10.44.

EXAMPLE 67

[1S-(1R*, 4R*, 5S*)]-N-(1-(4-imidazolylmethyl)-2-oxo-3-aza-4-phenylmethyl-5-hydroxy-6-(2-(1-t-butylamino-1-oxomethyl)-4-methylphenyl)-4-hexyl)-2-quinolinyl carboxamide The final coupling reaction was accomplished using an activated pentafluoro ester prepared according to the procedures described in Preparations 2 and 3.

Yield: 72 mg (31%) of a colorless solid.

$^1$H NMR (300 MHz, CDCl$_3$) d 1.45 (s, 9H), 2.26 (s, 3H), 2.73–2.80 (m, 2H), 2.94–2.99 (m, 2H), 3.13–3.23 (m, 2H), 3.90–3.95 (m, 1H), 4.29–4.40 (m, 1H), 4.89–4.97 (m, 1H), 6.68 (s, 1H), 6.79 (s, 1H), 6.85–7.15 (m, 10H), 7.49–7.60 (m, 3H), 7.72 (t, J=7.5 Hz, 1H), 7.79 (d, J=8 Hz, 1H), 8.03–8.14 (m, 2H), 8.18 (d, J=8 Hz, 1H), 8.85 (d, J=6.3 Hz, 1H).

EXAMPLE 68

[1S-(1R*, 4R*, 5S,)]-N-(1-(2-amino-2-oxoethyl)-2-oxo-3-aza-4-phenylmethyl-5-hydroxy-6-(2-(1-t-butylamino-1-oxomethyl)-5-isopropylphenyl)hexyl)-2-quinolinyl carboxamide The title compound was prepared according to the general procedure outlined in Example 1.

Yield: 85%.

$^1$H NMR (300 MHz, CDCl$_3$) d 1.20–1.30 (m, 6H), 1.45 (s, 9H), 2.60–3.20 (s, 7H), 3.70–3.80 (m, 1H), 4.25–4.40 (m, 1H), 4.90–5.00 (m, 1H), 5.50–6.20 (m, 4H), 6.80–7.30 (m, 9H), 7.55–8.30 (m, 6H), 9.15–3.05 (m, 1H).

MS (FD) 652 (M+100).

Analytical calc'd for C$_{38}$H$_{45}$N$_5$O$_5$: C 70.02, H 6.96, N 10.74; found C 69.83, H 6.98, N 10.62.

EXAMPLE 69

[1S-(1R*, 4R*, 5S*) ]-N-(1-(2-amino-2-oxoethyl)-2-oxo-3-aza-4-phenylmethyl-5-hydroxy-6-(2-(1-(1-methylcyclopent-1-yl)amino-1-oxomethyl)phenyl)hexyl)-2-quinolinyl carboxamide The title compound was prepared according to the general procedure outlined in Example 1.

The title compound was prepared according to the general procedure outlined in Example 1.

Yield: 36%

$^1$H NMR (300 MHz, DMSO-d$_6$) d 1.22 (s, 3H), 1.25–1.80 (m, 6H), 2.04–2.21 (m, 2H), 2.60–2.80 (m, 4H), 2.90–3.10 (m, 2H), 3.60–3.70 (m, 1H), 3.80–3.95 (m, 1H), 4.70–4.80 (m, 1H), 5.85 (d, 1H), 6.9–9.00 (m, 19H).

MS (FD) 636 (M+100).

Analytical calc'd for C$_{37}$H$_{41}$N$_5$O$_5$: C 69.90, H 6.50, N 11.02; found C 69.97, H 6.64, N 10.95.

EXAMPLE 70

[1S-(1R*, 4R*, 5*)]-N-(1-(2-(N-indol-3-ylmethyl)amino)-2-oxoethyl)-2-oxo-3-aza-4-phenylmethyl-5-hydroxy-6-(2-(1-t-butylamino-1-oxomethyl)phenyl)hexyl)-2-quinolinyl carboxamide The title compound was prepared according to the general procedure outlined in Example 51. Flash chromatography with 3–10% MeOH/CH$_2$Cl$_2$, followed by preparatory HPLC with 35% H$_2$O in MeOH afforded 0.087 g (48%) of a light yellow foam.

$^1$H NMR (300 MHz, (DMSO-d$_6$) d 1.35 (s, 9H), 2.61–2.74 (m, 4H), 2.92–3.04 (m, 2H), 3.60–3.65 (m, 1H), 3.86–3.89 (m, 1H), 4.30–4.34(m, 1H), 4.30–4.34 (m, 2H), 4.77–4.82 (m, 1H), 5.85 (d, J=5.5 Hz, 1H), 6.69 (t, J=7.4 Hz, 1H), 6.91–6.97 (m, 2H), 7.06 (t, J=7.4 Hz, 2H), 7.15–7.32 (m, 8H), 7.39 (d, J=7.9 Hz, 1H), 7.73 (t, J=7.8 Hz, 1H), 7.87 (t, j =7.8 Hz, 1H), 8.04 (d, J=9 Hz., 1H), 8.10 (d, J=8.5 Hz, 2H), 8.17 (d, J=8.5 Hz, 1H), 8.21 (br.s, 2H) 8.59 (d, J=8.5 Hz, 1H), 8.89 (d, J=8.1 Hz, 1H), 10.82 (s, 1H).

MS (FD) m/e 739 (M+1, 35), 738 (100). Analytical calc'd for C$_{44}$H$_{46}$N$_6$O$_5$·0.50H$_2$O: C 70.66, H 6.33, N 11.24; found C 70.28, H 6.32, N 10.98.

By substantially following the procedures described above one skilled in the art can prepare the compounds of Formula I.

As noted above, the compounds of the present invention are useful for inhibiting HIV protease which is associated with viral component production and assembly. A further embodiment of the present invention is a method of treating HIV infection comprising administering to a mammal in need of treatment an HIV inhibiting dose of a compound according to claim I or a pharmaceutically acceptable salt or solvate thereof. Another embodiment of the present invention is a method for inhibiting HIV replication by administering to a mammal infected with HIV, an HIV protease inhibiting dose (effective amount) of a compound according to Formula I or a pharmaceutically acceptable salt or solvate thereof.

The term "effective amount" as used herein, means an amount of a compound of the present invention which is capable of inhibiting the HIV protease mediated viral component production and assembly. The HIV protease inhibition contemplated by the present method includes both medical therapeutic and/or prophylactic treatment, as appropriate. The specific dose of compound administered according to this invention to obtain therapeutic and/or prophylactic effects will, of course, be determined by the particular circumstances surrounding the case, including, for example, the compound administered, the route of administration, and the condition being treated. A typical daily dose will contain a nontoxic dosage level of from about 0.01 mg/kg to about 50 mg/kg of body weight of an active compound of this invention. Preferred daily doses generally will be from about 0.05 mg/kg to about 20 mg/kg and ideally from about 0.1 mg/kg to about 10 mg/kg.

The compounds can be administered by a variety of routes including oral, rectal, transdermal, subcutaneous, intravenous, intramuscular, and intranasal. The compounds of the present invention are preferably formulated prior to administration. Therefore, another embodiment of the present invention is a pharmaceutical formulation comprising an effective amount of a compound of Formula I or a pharmaceutically acceptable salt thereof and a pharmaceutically acceptable carrier, diluent or excipient therefor.

The active ingredient in such formulations comprises from 0.1% to 99.9% by weight of the formulation. By "pharmaceutically acceptable" it is meant the carrier, diluent or excipient must be compatible with the other ingredients of the formulation and not deleterious to the recipient thereof.

The present pharmaceutical formulations are prepared by known procedures using well known and readily available ingredients. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), ointments containing, for example, up to 10% by weight of the active compound, soft and hard gelatin capsules, suppositories, sterile injectable solutions, sterile packaged powders, and the like.

The following formulation examples are illustrative only and are not intended to limit the scope of the invention in any way. "Active ingredient," of course, means a compound according to Formula I or a pharmaceutically acceptable salt thereof.

Formulation 1

Hard gelatin capsules are prepared using the following ingredients:

|  | Quantity (mg/capsule) |
| --- | --- |
| Active ingredient | 250 |
| Starch, dried | 200 |
| Magnesium stearate | 10 |
| Total | 460 mg |

Formulation 2

A tablet is prepared using the ingredients below:

|  | Quantity (mg/capsule) |
| --- | --- |
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg

Formulation 3

An aerosol solution is prepared containing the following components:

|  | Weight |
| --- | --- |
| Active ingredient | 0.25 |
| Ethanol | 25.75 |
| Propellant 22 (Chlorodifluoromethane) | 70.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4

Tablets, each containing 60 mg of active ingredient, are made as follows:

| Active ingredient | 60 mg |
| --- | --- |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |

| Talc | 1 mg |
| --- | --- |
| Total | 150 mg |

The active ingredient, starch and cellulose are passed through a No. 45 mesh U.S. sieve and mixed thoroughly. The aqueous solution containing polyvinyl-pyrrolidone is mixed with the resultant powder, and the mixture then is passed through a No. 14 mesh U.S. sieve. The granules so produced are dried at 50° C. and passed through a No. 18 mesh U.S. Sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules, each containing 80 mg of active ingredient, are made as follows:

| Active ingredient | 80 mg |
| --- | --- |
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation 6

Suppositories, each containing 225 mg of active ingredient, are made as follows:

| Active ingredient | 225 mg |
| --- | --- |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of active ingredient per 5 ml dose, are made as follows:

| Active ingredient | 50 mg |
| --- | --- |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

| Active ingredient | 100 mg |
|---|---|
| Isotonic saline | 1,000 ml |

The solution of the above ingredients generally is administered intravenously to a subject at a rate of 1 ml per minute.

The following experiments were carried out to demonstrate the ability of the compounds of the present invention to inhibit HIV protease.

The following abbreviations have the following meanings.

BSA—bovine serum albumin
BOC—t-butyloxycarbonyl
BrZ—2-bromobenzyloxycarbonyl
2-Clz—2-chlorobenzyloxycarbonyl
DCC—dicyclohexylcarbodiimide
DIEA—diisopropylethylamine
DMSO—dimethylsulfoxide
DTT—dithiothreitol
EDTA—ethylenediaminetetraacetic acid
FITC—fluorescein isothiocarbamyl
HEPES—4-(2-hydroxyethyl)-1-piperazineethanesulfonic acid
MES—4 morpholineethanesulfonic acid
PAM—phenylacetimidomethyl
TAPS—3-[tris(hydroxymethyl)methyl]amino-1-sulfonic acid
TRIS—tris(hydroxymethyl)aminomethane
TOS—p-toluenesulfonyl (tosyl)

Preparation of Substrate $N^\alpha$-Biotin-Gly-Ser-Gln-Asn-Tyr-Pro-Ile-Val-Gly-Lys(Nε-FITC)-OH

A. Preparation of $N^\alpha$-Biotin-Gly-Ser-Gln-Asn-Tyr-Pro-Ile-Val-Lys-OH

The protected peptide-resin $N^\alpha$-Boc-Gly-Ser-Gln-Asn-Tyr(BrZ)-Pro-Ile-Val-Gly-Lys(2-$C_1$Z)-OCH$_2$-PAM-resin was synthesized on an Advanced Chemtech Model 200 peptide synthesizer at 1.5 mmol scale using the standard double-couple protocol. The amino terminal Boc group was removed with 50% $CF_3COOH/CH_2Cl_2$ and the resulting resin neutralized with 5% diisopropylethylamine (DIEA) in $CH_2Cl_2$. Then 1.1 grams of biotin (4.5 mmol) was dissolved in 20 mL of dimethyl sulfoxide and the solution added to the peptide resin. Then, 4.5 mmol of DCC in 9 mL of $CH_2Cl_2$ was added to the resin and the reaction mixture brought to 40 mL total volume with 11 mL $CH_2Cl_2$. The coupling reaction was allowed to run for a total of 5 hours. The reaction solution was removed, the resin washed with DMSO, DMF and $CH_2Cl_2$, the resin neutralized with 5% DIEA in $CH_2Cl_2$, and the reaction repeated twice more with the reaction time being extended to 12 hours per reaction. Ninhydrin analysis of the resin indicated complete reaction of the biotin with the glycine amine group. The final peptide resin was washed extensively with DMF and $CH_2Cl_2$ and dried. Final yield =4.3 g (98% of theoretical).

B. Deprotection

The peptide was deprotected and cleaved from the resin using 50 ml of HF/m-cresol (9:1), 0° C., 1 hour. After removal of the HF by vacuum distillation, the m-cresol was extracted from the reaction mixture with 100 mL diethyl ether. The peptide was solubilized in 50% aqueous acetic acid, frozen and lyophilized. Final yield =2.14 g.

C. Purification

The crude $N^\alpha$-Biotin-Gly-Ser-Gln-Asn-Tyr-Pro-Ile-Val-Gly-Lys-OH was dissolved in 200 mL of 0.1% $CF_3COOH$ in 95:5 $H_2O:CH_3CN$, filtered through a 0.22 micron filter and applied to a 2.2×25 cm. reverse phase column of octadecyl-silica (vydac C-18) which had been equilibrated with the same buffer. The peptide was eluted with a 855 minute linear gradient of 7.5 to 25% $CH_3CN$ at 2 mL/minute with collection of fractions. Analytical high-performance liquid chromatography was performed on a 4.6×250 mm Vydac C-18 column using similar buffer conditions to analyze the column fractions. Column fractions containing the desired material were pooled, frozen and lyophilized. Final yield=1.206 g (62% of theory).

Amino acid analysis of the isolated $N^\alpha$-Biotin-Gly-Ser-Gln-Asn-Tyr-Pro-Ile-Val-Gly-Lys-OH gave the following ratios: Asn 1.1; Ser 0.96; Gln 1.1; Pro 1.1; Gly 2.1; Val 0.80; Ile 0.78; Tyr 1.1; Lys 1.1; in agreement with theory. Fast-atom bombardment mass spectrometry gave a molecular ion mass peak of 1288, in agreement with theory.

D. Labeling

The purified peptide was labeled as follows with a fluorescent marker at the C-terminal end for use in the assay. $N^\alpha$-Biotin-Gly-Ser-Gln-Asn-Tyr-Pro-Ile-Val-Gly-Lys-OH (1.206 g, 0.936 mmoles) was dissolved in 100 mL of 0.1M sodium borate, pH 9.5 with stirring. Then, 3 g of fluorescein isothiocyanate (7.7 mmol) was dissolved in 15 mL dimethyl sulfoxide and the solution added to the reaction in 10 equal portions over the course of a two hour period. The reaction was allowed to proceed for a further one hour after the final addition had been made. The pH of the solution was adjusted to 3 with 5N HCl. A precipitate formed which was removed from the reaction by centrifugation.

The pH of the remaining peptide solution was raised to 7.8 with 5N NaOH and the volume adjusted to 200 mL with 0.1M ammonium acetate, pH 7.5. The peptide solution was filtered through a 0.22 micron filter and loaded onto a 2.2×25 cm column of Vydac C-18 which had been equilibrated with 95:5 0.1M ammonium acetate, pH 7.5:$CH_3CN$. The peptide was eluted from the column with a 855 minute linear gradient of 5 to 25% $CH_3CN$, 2 mL/minute with collection of fractions. Analytical HPLC was used to identify fractions with the desired material, which were then pooled, frozen and lyophilized. Final yield =190.2 mg (12% of theoretical).

Amino acid analysis of the purified peptide gave the following: Asn 1.1; Ser 1.0; Gln 1.1: Pro 1.1; Gly 2.1; Val 0.8; Ile 0.8; Tyr 1.1; Lys 1.0; in agreement with theory. Fast-atom bombardment mass spectrometry gave a molecular ion mass peak of 1678, in agreement with theory.

The following describes the compositions of the reagents (buffers and solutions) used and referred to in the following evaluations.

| | |
|---|---|
| MES-ALB Buffer: | 0.05M 4-MES, pH 5.5 |
| | 0.02M NaCl |
| | 0.002M EDTA |
| | 0.001M DTT |
| | 1.0 mg/ml BSA |
| TBSA Buffer: | 0.02M TRIS |
| | 0.15M NaCl |
| | 1.0 mg/ml BSA |
| Avidin Coated Beads Solution: | 0.1% solution of Fluoricon Avidin Assay Particles (Avidin conjugated to solid polystyrene beads, 0.6–0.8 microns in diameter in TBSA Buffer |
| Enzyme Solution: | 27 IU/ml of purified HIV-1 protease in MES-ALB buffer (1 IU equals the amount of enzyme required to hydrolyze 1 μmol of substrate per minute at 37° C.) |

Fluorescence HIV-1 Protease Inhibitor Assay Procedure.

To each well of a round bottom, 96-well plate is added 20 μl of the Enzyme Solution followed by 10 μl of the compound to be evaluated in 20% aqueous DMSO. Purified HIV-1 protease was obtained as described below. The solution is incubated for one hour at room temperature and then 20 μl of a solution of the substrate $N^\alpha$-Biotin-Gly-Ser-Gln-Asn-Tyr-Pro-Ile-Val-Gly-Lys($N^\epsilon$-FITC)-OH, in MES-ALB buffer (1.5 μl/ml) is added to each well. The solutions are incubated for 16 hours at room temperature and thereafter to each well is added 150 μl of MES-ALB buffer.

To each well of a 96-well Pandex plate is added 25 μl of the Avidin Coated Beads Solution. Next, 25 μl of the diluted incubation solutions, described above, are added to each well of the Pandex plate. The solutions are mixed well and the plates are loaded into a Pandex® machine, washed, evacuated and read. Sample detection was performed by excitation at 485 nm and reading the resulting epifluorescence at 535 nm.

Inhibition of HIV-1 Protease Produced in E. coli.

The compounds of the present invention were also tested for their ability to block HIV protease processing of $Pr48^{gag}$ (a recombinant polyprotein containing p 17, p24 and p7).

A. Culture of E. coli K12 L507/DHP10D

Lyophils of E. coli K12 L507/pHP10D are obtained from the Northern Regional Research Laboratory, Peoria, Ill. 61604, under the accession number NRRL B-18560 (deposited Nov. 14, 1989). The lyophils are decanted into tubes containing 10 ml LB medium (10 g Bacto-tryptone, 5 g Bacto-yeast extract, and 10 g NaCl per liter; pH is adjusted to 7.5) and incubated at 32° C., overnight.

A small portion of the overnight culture was placed on LB-agar (LB medium with 15 g/l Bacto-agar) plates containing 12.5 μg/ml tetracycline in a manner so as to obtain a single colony isolate of E. coli K12 L507/pHP10D. The single colony obtained was inoculated into 10 ml of LB medium containing 12.5 μg/ml tetracycline and incubated overnight at 32° C. with vigorous shaking. The 10 ml overnight culture was inoculated into LB medium containing 12.5 μg/ml tetracycline and incubated at 32° C. with vigorous shaking until the culture reached mid-log phase.

B. Culture of E. coli K12 L507/pHGAG

Lyophils of E. coli K12 L507/pHGAG are obtained from the NRRL under the accession number NRRL B-18561 (deposited Nov. 14, 1989). A purified colony of E. coli K 12 L507/pHGAG was isolated, and used as an inoculum for a culture which was grown to mid-log phase in substantial accordance with the teaching of Step A above for E. Coli K12 L507/pHP10D.

C. Preparation of Protease and gag fractions

A culture of E. coli K12 L507/pHP10D was grown to mid-log phase at 32° C. in LB media containing 12.5 μg/ml tetracycline. The cultivation temperature was quickly elevated to 40° C. to induce gene expression, and the cells were allowed to grow for 2.5 hours at this temperature before the culture was quickly chilled on ice. The cells were centrifuged and the cell pellet was resuspended in 20 ml 50 mmol MES buffer (pH 6.0) containing 1 mmol EDTA, 1 mmol DTT, 1 mmol PMSF, and 10% glycerol (Buffer A). Cells were lysed by sonication using a Fischer Model 300 Dismembrator and a microtip probe. Following centrifugation at 27,000 x g, the supernatant was brought to 60 ml with Buffer A and loaded at 1 ml/min onto a QAE-Sepharose column (2.0×19 cm) at 4° C. equilibrated in Buffer A. The column was washed isocratically for 180 min and then eluted with a gradient of 0–1.0M NaCl in Buffer A over 120 min. Enzymatic activity was measured by HPLC using the synthetic peptide SQNYPIV as described in Margolin et al., Biochem. Biophys. Res. Commun., 167, 554–560 (1990); the production of the p1 peptide (SQNY) was measured.

Active fractions were pooled, made 1.2M in ammonium sulfate, and applied to a hexyl agarose column (2.0×18 cm) equilibrated in Buffer A containing 1.2M ammonium sulfate. The sample, in 125 ml (1.85 mg/ml), was loaded at a flow rate of 1 ml/min at 4° C. The column was washed with the equilibration buffer for 240 min (1 ml/min) following sample loading and then a reverse linear gradient of 1.2–0M ammonium sulfate in Buffer A was applied to the column over 120 min at the same flow rate. The column was then washed isocratically in Buffer A for 120 min. Active fractions were pooled, concentrated to 10 ml using an Amicon stirred cell with a YM-10 membrane, and applied at 1 ml/min to a MonoS cation exchange column (1.0×10 cm) equilibrated in Buffer A. After washing isocratically for 30 min, protease was eluted using a linear gradient of 0–0.45M NaCl in Buffer A over 40 min followed by an isocratic wash with Buffer A containing 0.45M NaCl over 30 min. Chromatography was performed at 25° C.

Pooled active fractions were concentrated to 200 ul using an Amicon stirred cell and a YM-10 membrane, and the protease was then applied to a Superose 6 size exclusion column equilibrated in Buffer A containing 0.1M NaCl. The column was washed isocratically in this buffer at a flow rate of 0.5 ml/min. HIV protease was eluted as a single peak.

QAE-Sepharose, and hexyl agarose were purchased from Sigma Chemical Company. Superose 6 and MonoS were products of Pharmacia. Buffers and reagents were obtained from Sigma.

In an analogous manner, a culture of E. coli K12 507/pHGAG was grown to mid-log phase at 32° C. then shifted to 40° C. for about 4 to 5 hours. The culture was chilled on ice and centrifuged, then the pellet was resuspended in 8 ml lysis buffer containing 5 mg/ml lysozyme. Lysis buffer was comprised of 50 mmol Tris-HCl (pH 7.8), 5 mmol EDTA, 1 mmol DTT, 100 mmol NaCl, 1 μg/ml E64 and 2 μg/ml aprotinin. The culture was incubated about 30 to 60 minutes at 4° C., then briefly sonicated in a Branson® Cell Disrupter at 60% power, for three 20 second bursts with chilling between each burst. The culture was then centrifuged at 15,000 g. The supernatant, which contains the unprocessed gag protein, was partially purified by size exclusion chromatography on a Sephadex G-50 column and stored at –20° C. in 50% glycerol and lysis buffer.

E. Western Blot Analysis of HIV Protease Inhibition Assay

About 10 to 20 B1 of the purified protease was preincubated with serial dilutions (100 nM-0.1 nM; five-fold serial dilutions) of the compound to be tested at room temperature for 30 minutes. About 2 μl of the gag polyprotein was then added and incubated at 37° C. for one hour.

Next, about 25 μl of the reaction was mixed with loading buffer and subjected to polyacrylamide gel electrophoresis on a 12.5% Laemmli gel under reducing conditions. The proteins were transferred onto a nitrocellulose filter using standard "Western Blot" electrophoresis at 500 mAmps for 35 minutes at room temperature. The filter was air-dried, then non-specific immunoreaction was blocked by washing the filter for 30 minutes at 4° C. in a solution of 3% non-fat dry milk powder in phosphate buffered saline (PBS).

Monoclonal antibodies against p17 and/or p24 (available from DuPont, Wilmington, Del.) were added to about 40 ml of a 3% milk/PBS solution to a final concentration of 2 μg/ml. The nitrocellulose filter was added to the antisera solution and slowly rocked for 2 hours at 4° C. The filter was then removed and washed 5 times with PBS, then the maturation of the gag gene was determined by reaction with $I^{125}$-labeled protein A or by reaction with biotinylated anti-mouse IgG antibodies (Vecta Stain®).

To run the $I^{125}$-labeled protein A reaction, about 10 μCi of $I^{125}$-labeled protein A was added to 100 ml of the 3% milk/PBS solution. The filter was rocked in this solution for 2 hours at 4° C., washed three times with PBS, then two times with PBS and 0.1% Tween 20. The filter was then air-dried and exposed to x-ray film for autoradiography.

The Vecta Stain® (Vector Laboratories, Burlingome, Calif.) procedure was performed according to the manufacturer's recommendations. Four drops of the biotinylated IgG was added to 40 mls of the 3% Milk/PBS solution, then the filter was rocked in this solution for 60 minutes at 4° C. The filter was washed five time with PBS, then rocked 30 to 60 minutes at 4° C. in Reagent ABC. Reagent ABC was prepared by adding 4 drops of Reagent A (Avidin DH) and 4 drops of Reagent B (biotinylated peroxidase) to 20 ml of 3% Milk/PBS. The filter was then washed five time with PBS, then the filter was developed by washing it for 5 to 10 minutes in 10 ml of PBS containing 0.02% $H_2O_2$ and 10 ml of 4-chloro-1 naphthol. When the color was fully developed, the filter was washed with distilled water and air-dried.

Following the procedure, it is simple to determine the activity of the HIV-1 protease compounds of the present invention. When the protease is fully active, the gag protein, is cleaved from the precursor gag form into mature p24 and p17 proteins, which are readily measured by their presence relative to the precursor protein. The addition of an HIV-1 protease inhibitor to the reaction prevents the maturation of the gag protein, an event which is easily determined using gel electrophoresis and Western Blotting.

The HIV-1 protease inhibition activity of the compounds of Formula I were tested using this method. The compound is diluted, then aliquots of the solution are added to the purified protease and the protease and compound are "pre-incubated" at room temperature for 30 minutes. The gag lysate, MES buffer, DTT and NaCl were then added to the proper final concentrations and the reaction mixture was incubated one hour at 37° C. The reaction mixtures were then electrophoresed, "Western Blotted" and developed to determine the inhibitory activity of the compounds. The activity of each compound was determined by the yield of p17 as measured by LKB Ultrascan XL Laser densitometer.

Using the yield of p17 in the absence of inhibitor as 100%, the percent inhibition of the test compounds at each dilution was determined.

The $IC_{50}$ results obtained in the Fluorescence Assay and Western Blot for the compounds of the present invention are set forth below in Table 1.

TABLE 1

| | Inhibitory Activity | |
|---|---|---|
| Example No. | Fluorescence Assay $IC_{50}$* in ng/ml | Western Blot $IC_{50}$ in nM |
| 1 | 1.0 | 0.8 |
| 2 | 2.1 | 50 |
| 3 | 18 | 60 |
| 4 | 2.9 | 2.7 |
| 5 | 8.4 | — |
| 6 | 140 | 700 |
| 7 | 18 | — |
| 8 | 3.0 | 1.5 |
| 9 | 8.6 | — |
| 10 | 59 | — |
| 11 | 10 | 340 |
| 12 | 500 | >1000 |
| 13 | 8 | 9 |
| 14 | 85 | 100 |
| 15 | 2.7 | 1.6 |
| 16 | 34 | 1.0 |
| 17 | 1.2 | 0.5 |
| 18 | 31 | — |
| 19 | 2.1 | — |
| 20 | 0.7 | — |
| 21 | 2.5 | — |
| 22 | 6.6 | — |
| 23 | 0.4 | — |
| 24 | 0.3 | — |
| 25 | 1.0 | — |
| 26 | 0.7 | — |
| 27 | 5.1 | — |
| 28 | 7.0 | — |
| 29 | 72 | — |
| 30 | 7.2 | — |
| 31 | 7.1 | — |
| 32 | 2.4 | — |
| 33 | 1.4 | — |
| 34 | 4.5 | — |
| 35 | 78 | — |
| 36 | 650 | — |
| 37 | 21 | — |
| 38 | 0.77 | — |
| 39 | 3.3 | — |
| 40 | 28 | — |
| 41 | 8 | — |
| 42 | 340 | — |
| 43 | 1.3 | — |
| 44 | 1.3 | — |
| 45 | 0.88 | — |
| 46 | 1.3 | — |
| 47 | 3.4 | — |
| 48 | 0.8 | — |
| 49 | 0.5 | — |
| 50 | 0.16 | — |
| 51 | 9.2 | — |
| 52 | 2.9 | — |
| 53 | 0.77 | — |
| 54 | 49 | — |
| 55 | 0.81 | — |
| 56 | 24.2 | — |
| 57 | 9.7 | — |
| 58 | 1.8 | — |
| 59 | 7.2 | — |
| 60 | 1.0 | — |
| 61 | 1.3 | — |
| 62 | 3.8 | — |
| 63 | 0.5 | — |
| 64 | 0.5 | — |
| 65 | 1.2 | — |
| 66 | 1.5 | — |

TABLE 1-continued

| | Inhibitory Activity | |
|---|---|---|
| Example No. | Fluorescence Assay IC$_{50}$* in ng/ml | Western Blot IC$_{50}$ in nM |
| 67 | 5 | — |
| 68 | 0.15 | — |
| 69 | 0.76 | — |
| 70 | 0.58 | — |

*IC$_{50}$ values for Examples 2–70 are standardized relative to Ex 1.

We claim:

1. A compound having the formula

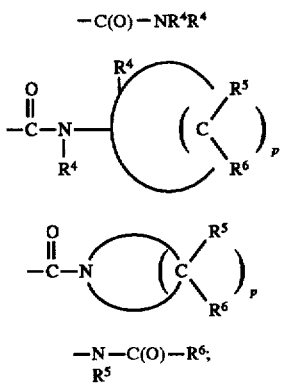

where $R^1$ is aryl or C$_5$–C$_7$ cycloalkyl;

$R^b$ is hydrogen or an amino protecting group;

Y is phenyl, substituted phenyl, naphthyl, substituted naphthyl, quinolinyl, furyl, phienyl, benzofuryl, or benzothienyl; and $R^3$ is a group having the structure;

1) —C(O)—NR$^4$R$^4$

2) 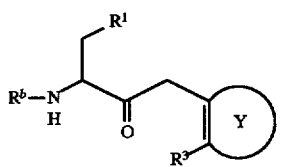

3) 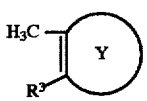

4) —N—C(O)—R$^6$;
   |
   R$^5$

5) —N—C(O)—NR$^4$R$^4$;
   |
   R$^4$

6) 

I is 3, 4, or 5;

p is 4 or 5;

$R^4$ at each occurrence is independently hydrogen, C$_1$–C$_6$ alkyl, or hydroxy (C$_1$–C$_4$) alkanediyl;

$R^5$ and $R^6$ are independently selected from hydrogen, hydroxy, C$_1$–C$_6$, alkyl, C$_1$–C$_6$ alkoxy, amino, C$_1$–C$_4$ alkylamino, hydroxy (C$_1$–C$_4$)-alkanediyl, carboxy, (C$_1$–C$_4$ alkoxy)carbonyl, aminocarbonyl, C$_1$–C$_4$ alkylaminocarbonyl or aryl or a pharmaceutically acceptable salt or solvate thereof.

2. A process for preparing a compound of claim 1 comprising:

a) reacting a compound having the Formula:

$$H_3C-\overset{R^3}{\underset{}{=}}\!\!\bigcirc\!\!-Y$$

where $R^3$ and Y are as defined above with a C$_1$–C$_4$ alkyl lithium or lithium di(C$_1$–C$_4$ alkyl) amide base optionally in the presence of a tetramethyl(C$_1$–C$_4$ alkylene)diamine catalyst in an aprotic solvent to afford the corresponding anion; and b) reacting the anion from (a) with an amide having the Formula $$R^b\!-\!\overset{H}{N}\!-\!\underset{R^1}{\overset{}{C}}\!-\!\overset{O}{\underset{}{C}}\!-\!\underset{OCH_3}{\overset{CH_3}{N}}$$

where $R^b$ and $R^1$ are as defined above in an aprotic solvent.

* * * * *

UNITED STATES PATENT AND TRADEMARK OFFICE
CERTIFICATE OF CORRECTION

PATENT NO. : 5,719,287
DATED : February 17, 1998
INVENTOR(S) : Kaldor, et al.

It is certified that error appears in the above-indentified patent and that said Letters Patent is hereby corrected as shown below:

Column 9, line 40, "$R^3$" should read --$R^{3a}$--.
Column 12, line 43, "Reactions" should read --Reactions 3 --.
Column 13, line 57, "multipier" should read --multiplet--.
Column 23, line 52, "MeOH/$CH_2C_{12}$)" should read --MeOH/$CH_2Cl_2$)--.

Signed and Sealed this

Third Day of November, 1998

Attest:

Attesting Officer

BRUCE LEHMAN

Commissioner of Patents and Trademarks